United States Patent
Ji et al.

(10) Patent No.: US 9,108,891 B1
(45) Date of Patent: Aug. 18, 2015

(54) ETHYLENE SEPARATION WITH PRESSURE SWING ADSORPTION

(71) Applicant: Chevron Phillips Chemical Company LP, The Woodlands, TX (US)

(72) Inventors: Lei Ji, Kingwood, TX (US); Ai-Fu Chang, Humble, TX (US)

(73) Assignee: Chevron Phillips Chemical Company, The Woodlands, TX (US)

( * ) Notice: Subject to any disclaimer, the term of this patent is extended or adjusted under 35 U.S.C. 154(b) by 0 days.

(21) Appl. No.: 14/550,638

(22) Filed: Nov. 21, 2014

(51) Int. Cl.
C07C 7/13 (2006.01)
C07C 7/04 (2006.01)
C07C 9/06 (2006.01)
C08F 2/12 (2006.01)
C07C 7/00 (2006.01)
C08F 10/02 (2006.01)

(52) U.S. Cl.
CPC . *C07C 7/005* (2013.01); *C07C 7/04* (2013.01); *C07C 7/13* (2013.01); *C08F 10/02* (2013.01)

(58) Field of Classification Search
CPC ............ C07C 7/005; C07C 7/04; C07C 7/13; C07C 9/06; C08F 10/02
USPC ............................................ 585/826; 526/64
See application file for complete search history.

(56) References Cited

U.S. PATENT DOCUMENTS

| 3,248,179 | A | 4/1966 | Norwood |
| 4,501,885 | A | 2/1985 | Sherk et al. |
| 4,588,790 | A | 5/1986 | Jenkins, III et al. |
| 5,352,749 | A | 10/1994 | DeChellis et al. |
| 5,436,304 | A | 7/1995 | Griffin et al. |
| 5,565,175 | A | 10/1996 | Hottovy et al. |
| 5,575,979 | A | 11/1996 | Hanson |
| 6,200,366 | B1 * | 3/2001 | Bulow et al. ............... 95/101 |
| 6,225,421 | B1 | 5/2001 | Promel et al. |
| 6,239,235 | B1 | 5/2001 | Hottovy et al. |
| 6,262,191 | B1 | 7/2001 | Hottovy et al. |
| 6,833,415 | B2 | 12/2004 | Kendrick et al. |

(Continued)

OTHER PUBLICATIONS

Böhme, Ulrike, et al., "Ethene/Ethane and Propene/Propane Separation via the Olefin and Paraffin Selective Metal-Organic Framework Adsorbents CPO-27 and ZIF•8," Langmuir, 2013, pp. 8592-8600, vol. 29, American Chemical Society.

(Continued)

*Primary Examiner* — Fred M Teskin
(74) *Attorney, Agent, or Firm* — Rodney B. Carroll; Conley Rose, P.C.; Monte Rhodes

(57) ABSTRACT

A process for component separation in a polymer production system comprising: (a) separating a polymerization product into a gas stream and a polymer stream; (b) processing the gas stream in distillation columns to yield a light hydrocarbon stream (LHS) comprising ethylene and ethane; (c) contacting LHS with a purged hydrocarbon adsorber to yield a loaded hydrocarbon adsorber and a non-adsorbed gas stream, wherein ethane is adsorbed by the purged hydrocarbon adsorber at a first pressure to yield adsorbed ethane, and wherein the non-adsorbed gas stream comprises recovered ethylene; (d) contacting the loaded hydrocarbon adsorber with a sweeping gas stream at a second pressure to yield an unloaded hydrocarbon adsorber and a recovered adsorbed gas stream comprising the sweeping gas stream and desorbed ethane; and (e) contacting the unloaded hydrocarbon adsorber with the sweeping gas stream at the first pressure to yield the purged hydrocarbon adsorber and a spent sweeping gas.

23 Claims, 6 Drawing Sheets

(56) References Cited

U.S. PATENT DOCUMENTS

| | | |
|---|---|---|
| 7,163,906 B2 | 1/2007 | McDaniel et al. |
| 7,572,943 B2 | 8/2009 | Elomari et al. |
| 7,572,944 B2 | 8/2009 | Elomari et al. |
| 7,576,252 B2 | 8/2009 | Elomari et al. |
| 7,619,047 B2 | 11/2009 | Yang et al. |
| 7,691,771 B2 | 4/2010 | Harris et al. |
| 7,732,363 B2 | 6/2010 | Elomari et al. |
| 7,732,364 B2 | 6/2010 | Chang et al. |
| 7,790,820 B2 | 9/2010 | Jensen et al. |
| 7,807,597 B2 | 10/2010 | Elomari et al. |
| 7,960,487 B2 | 6/2011 | Yang et al. |
| 8,017,825 B2 * | 9/2011 | Kuznicki et al. ............. 585/829 |
| 8,101,809 B2 | 1/2012 | Elomari et al. |
| 8,128,739 B1 | 3/2012 | Gupta |
| 8,192,709 B2 | 6/2012 | Reyes et al. |
| 8,222,471 B2 | 7/2012 | Elomari et al. |
| 8,314,245 B2 | 11/2012 | Yaghi et al. |
| 8,471,086 B2 | 6/2013 | Hommeltoft |
| 8,524,968 B2 | 9/2013 | Elomari et al. |
| 8,871,154 B2 | 10/2014 | Hommeltoft |
| 2009/0004417 A1 | 1/2009 | Follestad et al. |
| 2012/0165586 A1 | 6/2012 | Timken et al. |

OTHER PUBLICATIONS

Chmelik, Christian, et al., "Ethene/ethane mixture diffusion in the MOF sieve ZIF-8 studied by MAS PFG NMR diffusometry," Microporous and Mesoporous Materials, 2012, pp. 135-141, vol. 147, Elsevier Inc.

Gücüyener, Canan, et al., "Ethane/Ethene Separation Turned on Its Head: Selective Ethane Adsorption on the Metal-Organic Framework ZIF-7 through a Gate-Opening Mechanism," J. Am. Chem. Soc., 2010, pp. 17704-17706, vol. 132, No. 50, American Chemical Society.

* cited by examiner

US 9,108,891 B1

ETHYLENE SEPARATION WITH PRESSURE SWING ADSORPTION

TECHNICAL FIELD

The present disclosure generally relates to the production of polyethylene. More specifically, this disclosure relates to a process for improving polyethylene production efficiency by recovering unreacted ethylene.

BACKGROUND

The production of polymers such as polyethylene from light gases requires a high purity feedstock of monomers and comonomers. Due to the small differences in boiling points between the light gases in such a feedstock, industrial production of a high purity feedstock can require the operation of multiple distillation columns, high pressures, and cryogenic temperatures. As such, the energy costs associated with feedstock purification represent a significant proportion of the total cost for the production of such polymers. Further, the infrastructure required for producing, maintaining, and recycling high purity feedstock is a significant portion of the associated capital cost.

In order to offset some of the costs and maximize production, it can be useful to reclaim and/or recycle any unreacted feedstock gases, especially the light hydrocarbon reactants, such as ethylene. Gases comprising unreacted monomers can be separated from the polymer after the polymerization reaction. The polymer is processed while the unreacted monomers are recovered from the gases that are reclaimed following the polymerization reaction. To accomplish this, the reclaimed gas streams have conventionally either been routed through a purification process or redirected through other redundant processing steps. In either case, conventional processes of recovering monomer (e.g., unreacted ethylene) have necessitated energetically unfavorable and expensive processes. Thus, there is an ongoing need for developing efficient processes for the recovery of unreacted ethylene during polyethylene production.

BRIEF SUMMARY

Disclosed herein is a process for component separation in a polymer production system, the process comprising (a) separating a polymerization product stream into a gas stream and a polymer stream, (b) processing the gas stream in one or more distillation columns to yield a light hydrocarbon stream, wherein the light hydrocarbon stream comprises ethylene and ethane, (c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream, (d) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, and wherein the desorbed ethane comprises at least a portion of the adsorbed ethane, and (e) contacting at least a portion of the unloaded hydrocarbon adsorber with at least a portion of the sweeping gas stream at the first pressure to yield the purged hydrocarbon adsorber and a spent sweeping gas.

Also disclosed herein is a process for component separation in a polymer production system, the process comprising (a) separating a polymerization product stream into a gas stream and a polymer stream, (b) processing the gas stream in one or more distillation columns to yield a light hydrocarbon stream, wherein the light hydrocarbon stream comprises ethylene and ethane, (c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a pressure of from about 1,000 kPa to about 2,700 kPa to yield adsorbed ethane, wherein the non-adsorbed gas stream comprises recovered ethylene, wherein the recovered ethylene comprises at least a portion of the ethylene of the light hydrocarbon stream, wherein the light hydrocarbon stream is characterized by a temperature of from about −25° C. to about 30° C., wherein the hydrocarbon adsorber is characterized by an adsorption selectivity of ethane versus ethylene as determined by volumetric adsorption at 298 K and at a pressure of from about 1,000 kPa to about 2,700 kPa of equal to or greater than about 2, and wherein the hydrocarbon adsorber comprises a zeolitic imidazolate framework (ZIF) selected from ZIF-7, ZIF-8, or both ZIF-7 and ZIF-8, (d) contacting at least a portion of the loaded hydrocarbon adsorber with a sweeping gas stream at a pressure of from about 50 kPa to about 150 kPa to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the sweeping gas stream comprises isobutane and/or nitrogen, and (e) contacting at least a portion of the unloaded hydrocarbon adsorber with at least a portion of the sweeping gas stream at a pressure of from about 1,000 kPa to about 2,700 kPa to yield the purged hydrocarbon adsorber and a spent sweeping gas.

Further disclosed herein is a process for component separation in a polymer production system, the process comprising (a) separating a polymerization product stream into a gas stream and a polymer stream, (b) processing the gas stream in one or more distillation columns to yield a light hydrocarbon stream, wherein the light hydrocarbon stream comprises a first hydrocarbon and a second hydrocarbon, (c) contacting at least a portion of the light hydrocarbon stream with a purged hydrocarbon adsorber to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, and wherein the non-adsorbed gas stream comprises recovered second hydrocarbon, wherein the recovered second hydrocarbon comprises at least a portion of the second hydrocarbon of the light hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2, (d) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed first hydrocarbon, wherein the desorbed first hydrocarbon comprises at least a portion of the adsorbed first hydrocarbon, and wherein the first pressure is greater than the second pressure by equal to or greater than about 400 kPa, and (e) contacting at least a portion of the unloaded hydrocarbon adsorber with at least a portion of the sweeping gas stream at the first pressure to yield the purged hydrocarbon adsorber and a spent sweeping gas.

Further disclosed herein is a process for hydrocarbon recovery, the process comprising (a) providing a hydrocarbon stream comprising a first hydrocarbon and a second hydrocarbon, wherein the first hydrocarbon is a saturated hydrocarbon, and wherein the second hydrocarbon is an olefin, (b) contacting at least a portion of the hydrocarbon stream with a purged hydrocarbon adsorber to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, and wherein the non-adsorbed gas stream comprises recovered second hydrocarbon, wherein the recovered second hydrocarbon comprises at least a portion of the second hydrocarbon of the hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2, (c) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed first hydrocarbon, wherein the desorbed first hydrocarbon comprises at least a portion of the adsorbed first hydrocarbon, and wherein the first pressure is greater than the second pressure by equal to or greater than about 400 kPa, and (d) contacting at least a portion of the unloaded hydrocarbon adsorber with at least a portion of the sweeping gas stream at the first pressure to yield the purged hydrocarbon adsorber and a spent sweeping gas.

Further disclosed herein is a pressure swing adsorption system comprising at least two pressure swing adsorption units, wherein the at least two pressure swing adsorption units are operated in parallel, wherein the pressure swing adsorption unit comprises at least one hydrocarbon adsorber bed disposed therein, wherein the hydrocarbon adsorber bed comprises a hydrocarbon adsorber, wherein the hydrocarbon adsorber is contacted with a sweeping gas stream to yield a purged hydrocarbon adsorber, wherein the pressure swing adsorption unit adsorbs at a first pressure, wherein the purged hydrocarbon adsorber adsorbs a first hydrocarbon to yield a loaded hydrocarbon adsorber comprising an adsorbed first hydrocarbon and a non-adsorbed gas stream comprising a second hydrocarbon, wherein the hydrocarbon adsorber has an adsorption selectivity of the first hydrocarbon versus the second hydrocarbon as determined by volumetric adsorption at 298 K and at the first pressure of equal to or greater than about 2, wherein the pressure swing adsorption unit regenerates at a second pressure, wherein the loaded hydrocarbon adsorber is regenerated to yield an unloaded hydrocarbon adsorber, and a desorbed first hydrocarbon, wherein the first pressure is greater than the second pressure by equal to or greater than about 400 kPa, and wherein the unloaded hydrocarbon adsorber is contacted with a sweeping gas stream to yield a purged hydrocarbon adsorber.

Further disclosed herein is a process for ethylene polymerization, the process comprising (a) polymerizing ethylene in a slurry loop reactor system to obtain a polymerization product stream, (b) separating a polymerization product stream in a flash chamber into a gas stream and a polymer stream, (c) processing the gas stream in one or more distillation columns to yield a light hydrocarbon stream, wherein the light hydrocarbon stream comprises ethane and ethylene, (d) contacting at least a portion of the light hydrocarbon stream with a purged hydrocarbon adsorber to yield a loaded hydrocarbon adsorber and a non-adsorbed gas stream, wherein at least a portion of ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream, wherein the hydrocarbon adsorber is characterized by an adsorption selectivity of ethane versus ethylene as determined by volumetric adsorption at 298 K and at the first pressure of equal to or greater than about 2, (e) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the first pressure is greater than the second pressure by equal to or greater than about 400 kPa, and (f) contacting at least a portion of the unloaded hydrocarbon adsorber with at least a portion of the sweeping gas stream at the first pressure to yield the purged hydrocarbon adsorber and a spent sweeping gas.

Further disclosed herein is a process for hydrocarbon recovery, the process comprising (a) providing a hydrocarbon stream originating from a polymerization process, wherein the hydrocarbon stream comprises a first hydrocarbon and a second hydrocarbon, wherein the first hydrocarbon is a saturated hydrocarbon, and wherein the second hydrocarbon is an olefin, (b) loading a purged hydrocarbon adsorber with at least a portion of the first hydrocarbon to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, wherein the loaded hydrocarbon adsorber comprises the adsorbed first hydrocarbon, wherein the non-adsorbed gas stream comprises recovered second hydrocarbon, wherein the recovered second hydrocarbon comprises at least a portion of the second hydrocarbon of the hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2, (c) unloading the loaded hydrocarbon adsorber to yield an unloaded hydrocarbon adsorber and a recovered adsorbed gas stream, wherein a sweeping gas contacts at least a portion of the loaded hydrocarbon adsorber, wherein the adsorbed first hydrocarbon desorbs to yield a desorbed first hydrocarbon and the unloaded hydrocarbon adsorber, wherein the desorbed first hydrocarbon comprises at least a portion of the adsorbed first hydrocarbon, wherein the recovered adsorbed gas stream comprises at least a portion of the sweeping gas stream and at least a portion of the desorbed first hydrocarbon, and wherein the first pressure is greater than the second pressure by equal to or greater than about 400 kPa, and (d) purging the unloaded hydrocarbon adsorber with at least a portion of the sweeping gas stream at the first pressure to yield the purged hydrocarbon adsorber and a spent sweeping gas.

BRIEF DESCRIPTION OF THE DRAWINGS

For a detailed description of the preferred embodiments of the disclosed processes and systems, reference will now be made to the accompanying drawings in which.

DETAILED DESCRIPTION

Figure 1A:
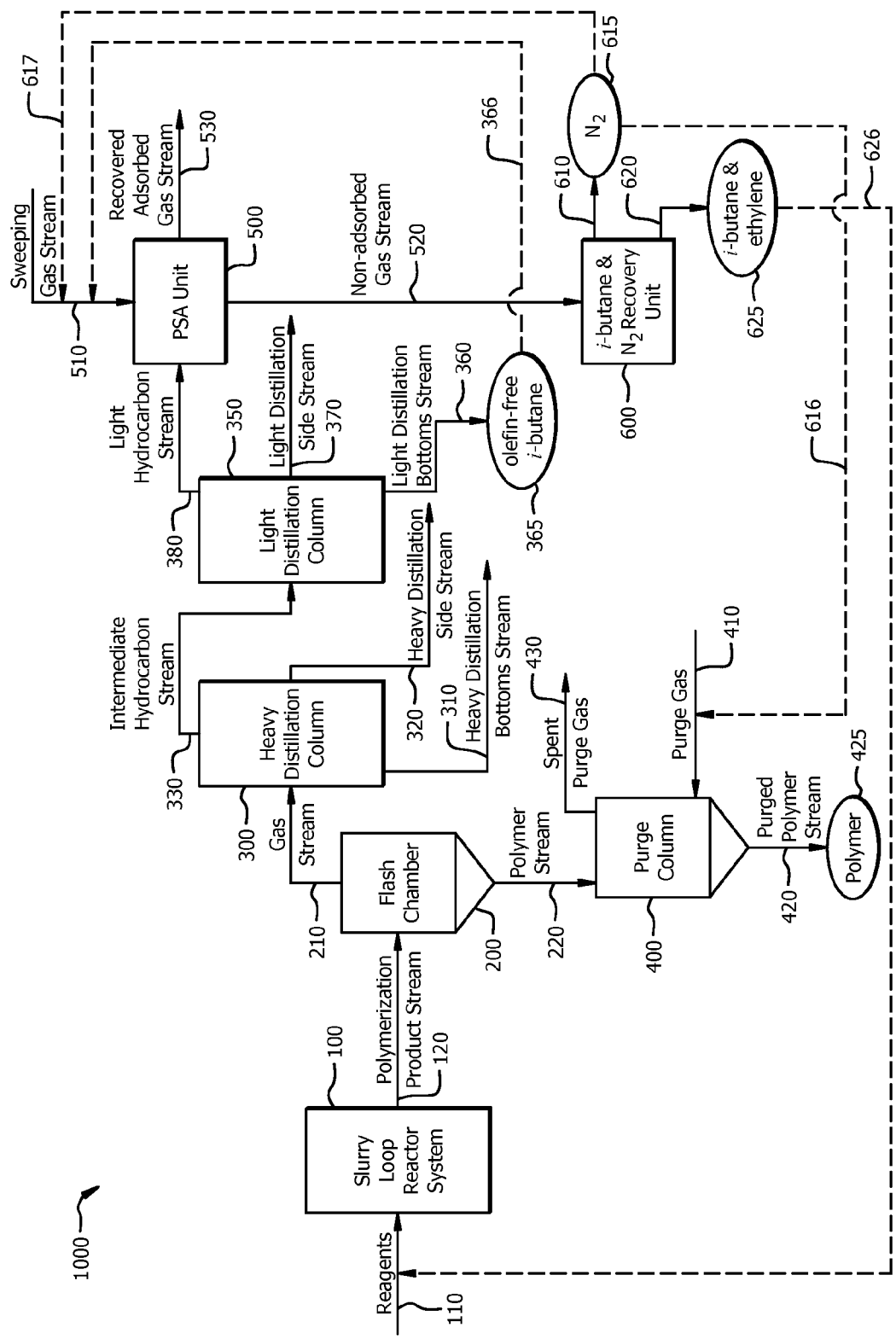
FIG. 1A illustrates a schematic of a first embodiment of a polyethylene production system.

It should be understood at the outset that although an illustrative implementation of one or more embodiments are provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, apparatuses, and processes related to petrochemical production processes, for example the production of polyethylene. The systems, apparatuses, and processes are generally related to the separation of a first chemical component or compound (e.g., unreacted monomer, unreacted ethylene) from a composition resulting from petrochemical production processes, for example the production of polyethylene, and comprising the first chemical component or compound and one or more other chemical components, compounds, or the like.

In an embodiment, a process for component separation in a polymer production system (e.g., polyethylene production system) can generally comprise the steps of (a) separating a polymerization product stream into a gas stream and a polymer stream; (b) processing the gas stream in one or more distillation columns to yield a light hydrocarbon stream, wherein the light hydrocarbon stream comprises ethylene and ethane; (c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream; (d) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, and wherein the desorbed ethane comprises at least a portion of the adsorbed ethane; and (e) contacting at least a portion of the unloaded hydrocarbon adsorber with at least a portion of the sweeping gas stream at the first pressure to yield the purged hydrocarbon adsorber and a spent sweeping gas.

In an embodiment, a process for component separation in a polymer production system (e.g., polyethylene production system) can generally comprise selectively separating a first hydrocarbon (e.g., by-product hydrocarbon, by-product ethane) from a second hydrocarbon (e.g., unreacted monomer, unreacted ethylene), wherein the first hydrocarbon and the second hydrocarbon can be recovered from a polymerization product stream. While the present disclosure will be discussed in detail in the context of a process for selectively separating hydrocarbons in a polyethylene production system, it should be understood that such process or any steps thereof can be applied in any suitable petrochemical production process requiring selective separation of hydrocarbons. The hydrocarbons can comprise any suitable hydrocarbons compatible with the disclosed methods and materials.

Referring to the embodiment of FIG. 1A, a first polyethylene production (PEP) system 1000 is disclosed. PEP system 1000 generally comprises a slurry loop reactor system 100, a flash chamber 200, a heavy distillation column 300, a light distillation column 350, a purge column 400, a pressure swing adsorption (PSA) unit 500, and an isobutane (i-butane) and nitrogen recovery unit (INRU) 600. In the PEP embodiments disclosed herein, various system components can be in fluid communication via one or more conduits (e.g., pipes, tubing, flow lines, etc.) suitable for the conveyance of a particular stream, for example as shown in detail by the numbered streams in FIG. 1A.

In an embodiment, a reagents stream 110 (also referred to as a feed stream) can be communicated to the slurry loop reactor system 100. A polymerization product stream 120 can be communicated from the slurry loop reactor system 100 to the flash chamber 200. A gas stream 210 can be communicated from the flash chamber 200 to the heavy distillation column 300. In some embodiments, the heavy distillation column 300 can be referred to as a first distillation column. A heavy distillation bottoms stream 310 can be emitted from the heavy distillation column 300, and a heavy distillation side stream 320 can be emitted from the heavy distillation column 300. An intermediate hydrocarbon stream 330 can be emitted from the heavy distillation column 300 and communicated to the light distillation column 350. In some embodiments, the light distillation column 350 can be referred to as a second distillation column. A light distillation side stream 370 can be emitted from the light distillation column 350. A light distillation bottoms stream 360 comprising olefin-free isobutane 365 can be emitted from the light distillation column 350. A light hydrocarbon stream 380 can be communicated from the light distillation column 350 to the PSA unit 500. A sweeping gas stream 510 can be communicated to the PSA unit 500. At least a portion of the olefin-free isobutane 365 can be recycled 366 to the PSA unit 500, for example via the sweeping gas stream 510. A recovered adsorbed gas stream 530 can be emitted from the PSA unit 500. A non-adsorbed gas stream 520 can be communicated from the PSA unit 500 to the INRU 600. A gas stream 610 comprising nitrogen 615 can be emitted from the INRU 600. At least a portion of the nitrogen 615 can be recycled 617 to the PSA unit 500, for example via the sweeping gas stream 510. A gas stream 620 comprising isobutane and ethylene 625 can be emitted from the INRU 600. At least a portion of the isobutane and ethylene 625 can be recycled 626 to the slurry loop reactor system 100, for example via the reagents stream 110. A polymer stream 220 can be communicated from the flash chamber 200 to the purge column 400. A purge gas stream 410 can be communicated to the purge column 400. A purged polymer stream 420 comprising a polymer 425 can be emitted from the purge column 400. A spent purge gas stream 430 can be emitted from the purge column 400. At least a portion of the nitrogen 615 can be recycled 616 to the purge column 400, for example via the purge gas stream 410.

For purposes of the disclosure herein an "olefin-free" hydrocarbon (e.g., olefin-free isobutane) refers to a hydrocarbon (e.g., isobutane) that can be free of olefins, alternatively, substantially free of olefins, alternatively, essentially free of olefins, or alternatively, consist or consist essentially of non-olefins. Generally, olefins or alkenes are unsaturated hydrocarbons containing at least one carbon-carbon double bond. For example, olefins can be present in a substantially olefin-free hydrocarbon (e.g., substantially olefin-free isobutane) in an amount of less than about 10% by total weight of the olefin-free hydrocarbon, alternatively, less than about 9%, alternatively, less than about 8%, alternatively, less than about 7%, alternatively, less than about 6%, alternatively, less than about 5%, alternatively, less than about 4%, alternatively, less than about 3%, alternatively, less than about 2%, alternatively, less than about 1.0%, alternatively, less than about 0.5%, alternatively, less than about 0.1%.

Figure 1B:
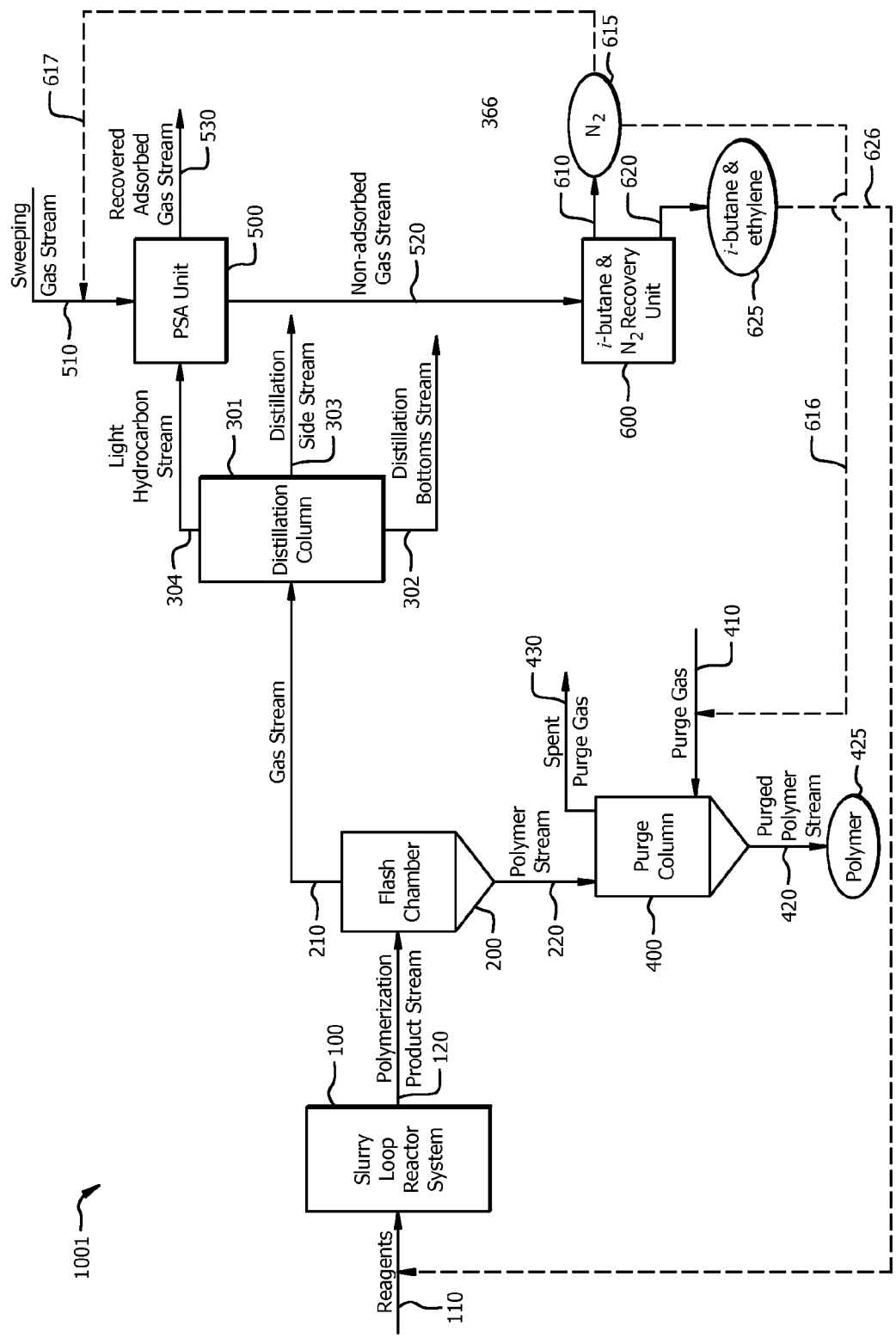
FIG. 1B illustrates a schematic of a second embodiment of a polyethylene production system.

Referring to the embodiment of FIG. 1B, a second PEP system 1001 is disclosed, which has a number of system components common with PEP system 1000. In the alternative embodiment illustrated by FIG. 1B, the second PEP system 1001 comprises one distillation column 301 (as opposed to two distillation columns 300 and 350 of PEP system 1000). Alternatively to the first PEP system 1000 (as illustrated in FIG. 1A), in the embodiment illustrated by FIG. 1B, the gas stream 210 can be communicated from the flash chamber 200 to the distillation column 301. A distillation side stream 303 can be emitted from the distillation column 301. A distillation bottoms stream 302 can be emitted from the distillation column 301. A light hydrocarbon stream 304 can be communicated from the distillation column 301 to the PSA unit 500.

Embodiments of a suitable PEP system having been disclosed, embodiments of a PEP process are now disclosed. One or more of the embodiments of a PEP process can be described with reference to one or more embodiments of PEP system 1000 and/or PEP system 1001. Although a given PEP process can be described with reference to one or more embodiments of a PEP system, such a disclosure should not be construed as so-limiting. Although the various steps of the processes disclosed herein may be disclosed or illustrated in a particular order, such should not be construed as limiting the performance of these processes to any particular order unless otherwise indicated.

Figure 2:
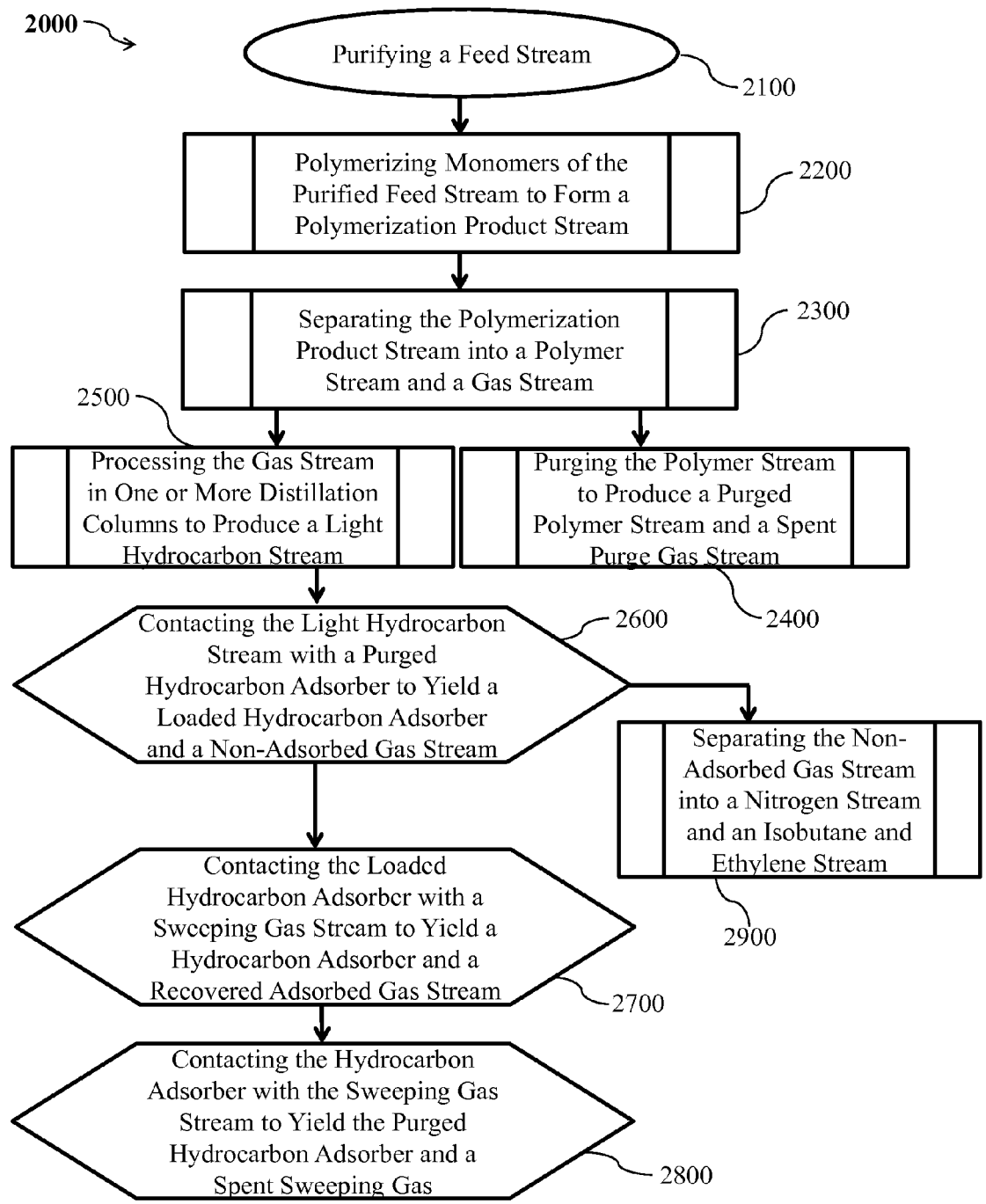
FIG. 2 illustrates a flow diagram of an embodiment of a polyethylene production process.

Referring to the embodiment of FIG. 2, a PEP process 2000 is illustrated. PEP process 2000 can generally comprise (i) a step 2100 of purifying a feed stream; (ii) a step 2200 of polymerizing monomers of the purified feed stream to form a polymerization product stream; (iii) a step 2300 of separating the polymerization product stream into a polymer stream and a gas stream; (iv) a step 2400 of purging the polymer stream to produce a purged polymer stream and a spent purge gas stream; (v) a step 2500 of processing the gas stream in one or more distillation columns to produce a light hydrocarbon stream; (vi) a step 2600 of contacting the light hydrocarbon stream with a purged hydrocarbon adsorber to yield a loaded hydrocarbon adsorber and a non-adsorbed gas stream; (vii) a step 2700 of contacting the loaded hydrocarbon adsorber with a sweeping gas stream to yield a hydrocarbon adsorber and a recovered adsorbed gas stream; (viii) a step 2800 of contacting the hydrocarbon adsorber with the sweeping gas stream to yield the purged hydrocarbon adsorber and a spent sweeping gas; and (ix) a step 2900 of separating the non-adsorbed gas stream into a nitrogen stream and an isobutane and ethylene stream. For purposes of the disclosure herein, step 2600 of contacting the light hydrocarbon stream with a purged hydrocarbon adsorber can also be referred to as an "adsorption step;" step 2700 of contacting the loaded hydrocarbon adsorber with a sweeping gas stream can also be referred to as a "desorption step;" and step 2800 of contacting the hydrocarbon adsorber with the sweeping gas stream can also be referred to as a "purging step." As will be disclosed later herein, a compound (e.g., first hydrocarbon, ethane, etc.) can be selectively adsorbed by a hydrocarbon adsorber in adsorption step 2600 to yield an adsorbed compound (e.g., adsorbed first hydrocarbon, adsorbed ethane, etc.); the adsorbed compound can be desorbed during desorption step 2700; and the hydrocarbon adsorber can be purged in purging step 2800.

In an embodiment, the PEP process 2000 or a portion thereof can be implemented via the PEP system 1000 (e.g., as illustrated in FIG. 1A) and/or the PEP system 1001 (e.g., as illustrated in FIG. 1B). In an embodiment, the PEP process 2000 is a continuous process.

In an embodiment, the PEP process 2000 can generally comprise the step 2100 of purifying a feed stream or a reagents stream. In one or more of the embodiments disclosed herein, purifying a feed stream can comprise separating unwanted compounds and elements from a feed stream comprising ethylene to form a purified feed stream. In an embodiment, purifying a feed stream can comprise any suitable method or process, including the non-limiting examples of filtering, membrane screening, reacting with various chemicals, absorbing, adsorbing, distillation(s), or combinations thereof.

Figure 3:
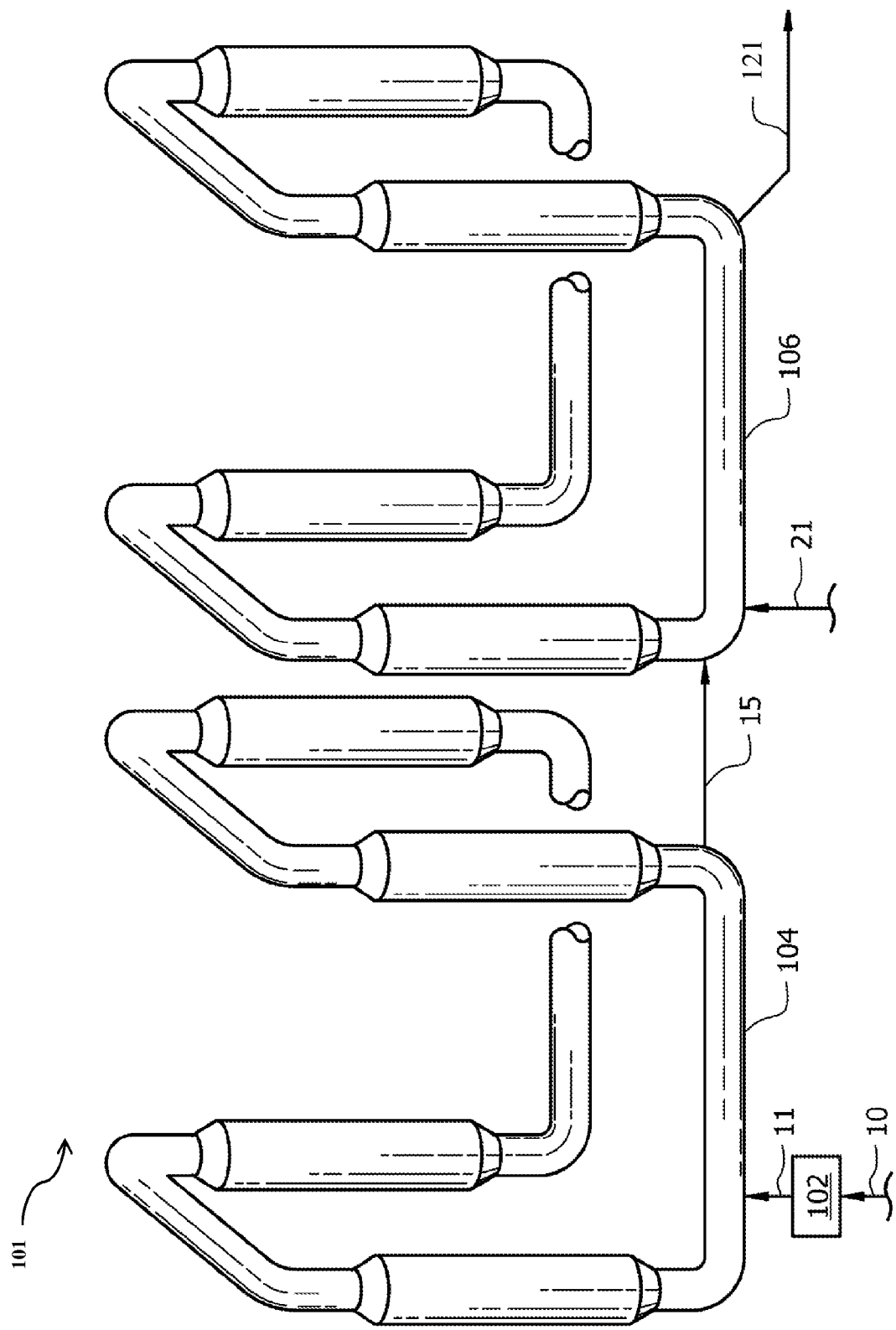
FIG. 3 illustrates a schematic of an embodiment of a slurry loop reactor system.

Referring to the embodiment of FIG. 3, a feed stream 10 (e.g., reagents stream 110 in the embodiments of FIG. 1A and/or FIG. 1B) can be communicated to a purifier 102. In an embodiment, the feed stream 10 can comprise ethylene and various other gases, such as but not limited to methane, ethane, acetylene, propane, propylene, water, nitrogen, oxygen, various other gaseous hydrocarbons having three or more carbon atoms, various contaminants, or combinations thereof. In one or more of the embodiments disclosed herein, the purifier 102 can comprise a device or apparatus suitable for the purification of one or more reactant gases in a feed stream comprising a plurality of potentially unwanted gaseous compounds, elements, contaminants, and the like. Non-limiting examples of a suitable purifier 102 can comprise a filter, a membrane, a reactor, an absorbent, a molecular sieve, one or more distillation columns, or combinations thereof. The purifier 102 can be configured to separate ethylene from a stream comprising a plurality of potentially unwanted gaseous compounds, elements, contaminants, and the like.

In an embodiment, purifying a feed stream can yield a purified feed stream 11 comprising substantially pure monomers (e.g., substantially pure ethylene). In an embodiment, the purified feed stream can comprise less than about 25% by total weight of the stream, alternatively, less than about 10%, alternatively, less than about 1.0% of any one or more of nitrogen, oxygen, methane, ethane, propane, comonomers, or combinations thereof. As used herein "substantially pure ethylene" refers to a fluid stream comprising at least about 60% ethylene, alternatively, at least about 70% ethylene, alternatively, at least about 80% ethylene, alternatively, at least about 90% ethylene, alternatively, at least about 95% ethylene, alternatively, at least about 99% ethylene by total weight of the stream, alternatively, at least about 99.5% ethylene by total weight of the stream. In an embodiment, the feed stream 11 can further comprise trace amounts of ethane, for example, as from a recycled stream, as will be discussed in more detail later herein.

In some embodiments, the purified feed stream can comprise a comonomer, such as unsaturated hydrocarbons having from 3 to 20 carbon atoms. Nonlimiting examples of comonomers that can be present in the purified feed stream include alpha olefins, such as for example propylene, 1-butene, 1-pentene, 1-hexene, 3-methyl-1-butene, 4-methyl-1-pentene, 1-heptene, 1-octene, 1-nonene, 1-decene, and the like, or combinations thereof.

In an embodiment, the PEP process 2000 can generally comprise the step 2200 of polymerizing monomers of the purified feed stream to form a polymerization product stream. The polymerization product stream can be formed using any suitable olefin polymerization method which can be carried out using various types of polymerization reactors.

As used herein, the terms "polymerization reactor" or "reactor" include any polymerization reactor capable of polymerizing olefin monomers or comonomers to produce homopolymers or copolymers. Such homopolymers and copolymers are referred to as resins or polymers. The various types of reactors include those that can be referred to as batch, slurry, gas-phase, solution, high pressure, tubular or autoclave reactors. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes could use intermittent or continuous product discharge. Processes can also include partial or full direct recycle of unreacted monomer, unreacted comonomer, and/or diluent. As will be appreciated by one of skill in the art, and with the help of this disclosure, the reactors considered for this disclosure could be any reactors that are part of a polymerization process that can yield a vent stream containing ethylene and ethane.

Polymerization reactor systems of the present disclosure can comprise one type of reactor in a system or multiple reactors of the same or different type. Production of polymers in multiple reactors can include several stages in at least two separate polymerization reactors interconnected by transfer stream(s), line(s), apparatus(es) (for example, a separation vessel(s)) and/or device(s) (for example, a valve or other mechanism) making it possible to transfer the polymers resulting from a first polymerization reactor into a second reactor. The desired polymerization conditions in one of the reactors can be different from the operating conditions of the other reactors. Alternatively, polymerization in multiple reactors can include the manual transfer of polymer from one reactor to subsequent reactors for continued polymerization. Multiple reactor systems can include any combination including, but not limited to, multiple loop reactors, multiple gas reactors, a combination of loop and gas reactors, multiple high pressure reactors or a combination of high pressure with loop and/or gas reactors. The multiple reactors can be operated in series or in parallel.

According to one aspect of this disclosure, the polymerization reactor system can comprise at least one loop slurry reactor comprising vertical or horizontal loops. Monomer, diluent, catalyst, and optionally any comonomer can be continuously fed to a loop reactor where polymerization occurs. Generally, continuous processes can comprise the continuous introduction of a monomer, an optional comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including but not limited to, flashing that can include any combination of heat addition and pressure reduction; separation by cyclonic action in either a cyclone or hydrocyclone; or separation by centrifugation.

A suitable slurry polymerization process (also known as the particle form process), is disclosed, for example, in U.S. Pat. Nos. 3,248,179; 4,501,885; 5,565,175; 5,575,979; 6,239,235; 6,262,191; and 6,833,415; each of which is incorporated by reference herein in its entirety.

In one or more embodiments, suitable diluents used in slurry polymerization include, but are not limited to, the monomer, and optionally, the comonomer, being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used.

According to yet another aspect of this disclosure, the polymerization reactor can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Likewise, copolymer product can optionally be withdrawn from the reactor and new or fresh comonomer can be added to replace polymerized comonomer, polymerized monomer, or combinations thereof. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. Gas phase reactors are disclosed in U.S. Pat. Nos. 5,352,749; 4,588,790; and 5,436,304; each of which is incorporated by reference herein in its entirety.

According to still another aspect of this disclosure, a high pressure polymerization reactor can comprise a tubular reactor or an autoclave reactor. Tubular reactors and/or autoclave reactors can have several zones where fresh monomer (optionally, comonomer), initiators, or catalysts can be added. Monomer (optionally, comonomer) can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to still yet another aspect of this disclosure, the polymerization reactor can comprise a solution polymerization reactor wherein the monomer (optionally, comonomer) can be contacted with the catalyst composition by suitable stirring or other means. A carrier comprising an inert organic diluent or excess monomer (optionally, comonomer) can be employed. If desired, the monomer and/or optional comonomer can be brought in the vapor phase into contact with the catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactors suitable for the disclosed systems and processes can further comprise any combination of at least one raw material feed system, at least one feed system for catalyst or catalyst components, and/or at least one polymer recovery system. Suitable reactor systems can further comprise systems for feedstock purification, catalyst storage and preparation, extrusion, reactor cooling, polymer recovery, fractionation, recycle, storage, loadout, laboratory analysis, and process control.

Conditions (e.g., polymerization conditions) that are controlled for polymerization efficiency and to provide resin properties include temperature, pressure, type and/or quantity of catalyst or co-catalyst, and concentrations and/or partial pressures of various reactants.

Polymerization temperature can affect catalyst productivity, polymer molecular weight and molecular weight distribution. Suitable polymerization temperature can be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1,000 psig. Pressure for gas phase polymerization is usually at about 200 psig to about 500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) can offer advantages. In an embodiment, polymerization can occur in an environment having a suitable combination of temperature and pressure. For example, polymerization can occur at a pressure in a range of from about 550 psi to about 650 psi, alternatively, from about 600 psi to about 625 psi and a temperature in a range of from about 170° F. to about 230° F., alternatively, from about 195° F. to about 220° F.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological parameters.

The concentrations and/or partial pressures of monomer, comonomer, hydrogen, co-catalyst, modifiers, and electron donors are important in producing these resin properties. Comonomer can be used to control product density. Hydrogen can be used to control product molecular weight. Cocatalysts can be used to alkylate, scavenge poisons and control molecular weight. Modifiers can be used to control product properties and electron donors affect stereoregularity, the molecular weight distribution, and/or molecular weight. In addition, the concentration of poisons is minimized because poisons impact the reactions and product properties.

In an embodiment, any suitable catalyst system can be employed. A suitable catalyst system can comprise a catalyst and, optionally, a co-catalyst (e.g., organoaluminum compound) and/or promoter. Non-limiting examples of suitable catalyst systems include Ziegler Natta catalysts, Ziegler catalysts, chromium catalysts, chromium oxide catalysts, chrome-silica catalysts, chrome-titania catalysts, chromocene catalysts, metallocene catalysts, nickel catalysts, or combinations thereof. Catalyst systems suitable for use in the present disclosure have been described, for example, in U.S. Pat. Nos. 7,163,906; 7,619,047; 7,790,820; and 7,960,487 and U.S. Patent Application Publication No. 2009/0004417, each of which is incorporated by reference herein in its entirety.

In an embodiment of the present disclosure, the catalyst system can comprise an activator. The activator can be a solid oxide activator-support, a chemically treated solid oxide, a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, an aluminoxane, a supported aluminoxane, an ionizing ionic compound, an organoboron compound, or any combination thereof. The terms "chemically-treated solid oxide," "solid oxide activator-support," "acidic activator-support," "activator-support," "treated solid oxide compound," and the like are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises the calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition.

In one or more of the embodiments disclosed herein, monomers in a feed stream (e.g., purified feed stream 11) can be polymerized. In one or more embodiments, polymerizing monomers of the purified feed stream can comprise allowing a polymerization reaction between a plurality of monomers by contacting a monomer or monomers with a catalyst system under conditions suitable for the formation of a polymer. In one or more of the embodiments disclosed herein, polymerizing comonomers of the purified feed stream can comprise allowing a polymerization reaction between a plurality of comonomers by contacting a comonomer or comonomers with a catalyst system under conditions suitable for the formation of a copolymer.

In an aspect of this disclosure, the step 2200 of polymerizing monomers of the purified feed stream to form a polymerization product stream can be carried out using a slurry loop reactor system, such as for example a slurry loop reactor system 101 illustrated in the embodiment of FIG. 3. The slurry loop reactor system 101 generally comprises a purifier 102, a first reactor 104, and a second reactor 106. In the slurry loop reactor system embodiments disclosed herein, various system components can be in fluid communication via one or more conduits (e.g., pipes, tubing, flow lines, etc.) suitable for the conveyance of a particular stream, for example as shown in detail by the numbered streams in FIG. 3.

In an embodiment, a purified feed stream 11 can be communicated from the purifier 102 to one or more of the reactors (e.g., a first reactor 104, a second reactor 106). Where the slurry loop reactor system comprises two or more reactors, a mid-polymerization reactor stream 15 can be communicated from the first reactor 104 to the second reactor 106. Hydrogen can be introduced into the second reactor 106 in stream 21. A polymerization product stream (e.g., polymerization product stream 121 in FIG. 3, polymerization product stream 120 in FIG. 1A and/or FIG. 1B) can be emitted from the first reactor 104 and/or the second reactor 106.

In embodiments as illustrated by FIG. 3, polymerizing monomers of the purified feed stream can comprise routing the purified feed stream 11 to the one or more of the polymerization reactors 104, 106. Polymerizing monomers of the mid-polymerization reactor stream 15 can comprise routing the mid-polymerization reactor stream 15 to polymerization reactor(s) 106. In embodiments as illustrated by FIG. 3, polymerizing monomers of the mid-polymerization reactor stream 15 can comprise routing the mid-polymerization reactor stream 15 from polymerization reactor(s) 104 to polymerization reactor(s) 106.

In one or more of the embodiments disclosed herein, the polymerization reactors 104, 106 can comprise any vessel or combination of vessels suitably configured to provide an environment for a chemical reaction (e.g., a contact zone) between monomers (e.g., ethylene) and/or polymers (e.g., an "active" or growing polymer chain), and optionally comonomers and/or copolymers, in the presence of a catalyst to yield a polymer (e.g., a polyethylene polymer) and/or copolymer. Although the embodiments illustrated in FIG. 3 illustrate a PEP system having two reactors in series, one of skill in the art viewing this disclosure will recognize that one reactor, alternatively, any suitable number and/or configuration of reactors, can be employed.

In embodiments as illustrated in FIG. 3, production of polymers in multiple reactors can include at least two polymerization reactors 104, 106 interconnected by one or more devices or apparatus (e.g., valve, continuous take-off valve, and/or continuous take-off mechanism). In embodiments as illustrated in FIG. 3, production of polymers in multiple reactors can include at least two polymerization reactors 104, 106 interconnected by one or more streams or lines (e.g., mid-polymerization reactor stream 15). In some embodiments, production of polymers in multiple reactors can include at least two polymerization reactors 104, 106 interconnected by one or more separators (e.g., flash chambers).

In an embodiment, polymerizing monomers can comprise introducing a suitable catalyst system into the first and/or second reactor 104, 106, respectively, so as to form a slurry. Alternatively, a suitable catalyst system can reside in the first and/or second reactor 104, 106, respectively.

As previously described herein, polymerizing monomers can comprise selectively manipulating one or more polymerization reaction conditions to yield a given polymer product, to yield a polymer product having one or more desirable properties, to achieve a desired efficiency, to achieve a desired yield, the like, or combinations thereof. In an embodiment, polymerizing monomers of the purified feed stream 11 can comprise adjusting one or more polymerization reaction conditions.

In an embodiment, polymerizing monomers can comprise maintaining a suitable temperature, pressure, and/or partial pressure(s) during the polymerization reaction, alternatively, cycling between a series of suitable temperatures, pressures, and/or partial pressure(s) during the polymerization reaction.

In an embodiment, polymerizing monomers can comprise polymerizing comonomers in one or more of polymerization reactors 104, 106. In an embodiment, polymerizing monomers can comprise introducing ethylene monomer and/or a comonomer to the polymerization reactor 106.

In an embodiment, polymerizing monomers can include introducing hydrogen into one or more of reactors 104 and 106. For example, FIG. 3 illustrates hydrogen can be introduced into reactor 106 through stream 21. The amount of hydrogen introduced into the reactor 106 can be adjusted so as to obtain, in the diluent, a molar ratio of hydrogen to ethylene of 0.001 to 0.1. This molar ratio can be at least 0.004 in reactor 106. In some embodiments, this molar ratio cannot exceed 0.05. The ratio of the concentration of hydrogen in the diluent in reactor 104 to the concentration of hydrogen polymerization reactor 106 can be at least 20, alternatively, at least 30, alternatively, at least 40, alternatively, not greater than 300, alternatively, not greater than 200. Suitable hydrogen concentration control methods and systems are disclosed in U.S. Pat. No. 6,225,421, which is incorporated by reference herein in its entirety.

In an embodiment, polymerizing monomers can comprise circulating, flowing, cycling, mixing, agitating, or combinations thereof, the monomers (optionally, comonomers), catalyst system, and/or the slurry within and/or between the reactors 104, 106. In an embodiment where the monomers (optionally, comonomers), catalyst system, and/or slurry are circulated, circulation can be at a velocity (e.g., slurry velocity) of from about 1 m/s to about 30 m/s, alternatively, from about 2 m/s to about 17 m/s, or alternatively, from about 3 m/s to about 15 m/s.

In some embodiments, polymerizing monomers can comprise configuring reactors 104, 106 to yield an unimodal resin. Herein, the "modality" of a polymer resin refers to the form of its molecular weight distribution curve, i.e., the appearance of the graph of the polymer weight fraction as a function of its molecular weight. The polymer weight fraction refers to the weight fraction of molecules of a given size. A polymer having a molecular weight distribution curve showing a single peak can be referred to as a unimodal polymer, a polymer having curve showing two distinct peaks can be referred to as bimodal polymer, a polymer having a curve showing three distinct peaks can be referred to as trimodal polymer, etc.

In other embodiments, polymerizing monomers can comprise configuring reactors 104, 106 to yield a multimodal (e.g., a bimodal) polymer (e.g., polyethylene). For example, the resultant polymer can comprise both a relatively high molecular weight, low density (HMWLD) polyethylene polymer and a relatively low molecular weight, high density (LMWHD) polyethylene polymer. For example, various types of suitable polymers can be characterized as having a various densities. For example, a Type I polymer can be characterized as having a density in a range of from about 0.910 g/cm$^3$ to about 0.925 g/cm$^3$, alternatively, a Type II polymer can be characterized as having a density from about 0.926 g/cm$^3$ to about 0.940 g/cm$^3$, alternatively, a Type III polymer can be characterized as having a density from about 0.941 g/cm$^3$ to about 0.959 g/cm$^3$, alternatively, a Type IV polymer can be characterized as having a density of greater than about 0.960 g/cm$^3$.

In the embodiments illustrated in FIG. 3, polymerizing monomers of the purified feed stream 11 can yield polymerization product stream 121. In an embodiment, the polymerization product stream 121 (e.g., polymerization product stream 120 in FIG. 1A and/or FIG. 1B) can generally comprise various solids, semi-solids, volatile and nonvolatile liquids, gases and combinations thereof. Polymerizing monomers of the purified feed stream 11 can yield the polymerization product stream 121 generally comprising unreacted monomer (e.g., ethylene), optional unreacted comonomer, by-products (e.g., ethane, which can be by-product ethane formed from ethylene and hydrogen), and a polymerization product (e.g., polymer and optionally, copolymer). As used herein, an "unreacted monomer," for example, ethylene, refers to a monomer that was introduced into a polymerization reactor during a polymerization reaction but was not incorporated into a polymer. As used herein, an "unreacted comonomer" refers to a comonomer that was introduced into a polymerization reactor during a polymerization reaction but was not incorporated into a polymer. The solids and/or liquids of the polymerization product stream 121 can comprise a polymer product (e.g., a polyethylene polymer), often referred to at this stage of the PEP process as "polymer fluff." The gases of the polymerization product stream 121 can comprise unreacted, gaseous reactant monomers or optional comonomers (e.g., unreacted ethylene monomers, unreacted comonomers), gaseous waste products, gaseous contaminants, or combinations thereof.

In an embodiment, the polymerization product stream 121 can comprise hydrogen, nitrogen, methane, ethylene, ethane, propylene, propane, butane, 1-butene, isobutane, pentane, hexane, 1-hexene and heavier hydrocarbons. In an embodiment, ethylene can be present in a range of from about 0.1% to about 15%, alternatively, from about 1.5% to about 5%, alternatively, about 2% to about 4% by total weight of the polymerization product stream. Ethane can be present in a range of from about 0.001% to about 4%, alternatively, from about 0.2% to about 0.5% by total weight of the polymerization product stream. Isobutane can be present in a range from about 80% to about 98%, alternatively, from about 92% to about 96%, alternatively, about 95% by total weight of the polymerization product stream.

In an embodiment, the PEP process 2000 can generally comprise the step 2300 of separating the polymerization product stream into a polymer stream and a gas stream. In one or more of the embodiments disclosed herein, separating the polymerization product into a polymer stream and a gas stream can generally comprise removing gases from liquids and/or solids (e.g., the polymer fluff) by any suitable process.

In embodiments as illustrated by FIG. 1A and/or FIG. 1B, separating the polymerization product into a polymer stream and a gas stream can comprise routing the polymerization product stream 120 to a separator (e.g., flash chamber 200). In some embodiments, the polymerization product stream 120 can comprise at least a portion of the polymerization product stream 121 emitted from the second reactor 106. In other embodiments, the polymerization product stream 120 can comprise at least a portion of the mid-polymerization reactor stream 15 emitted from the first reactor 104. In yet other embodiments, the polymerization product stream 120 can comprise at least a portion of the polymerization product stream 121 and at least a portion of the mid-polymerization reactor stream 15.

In one or more of the embodiments disclosed herein, a separator such as flash chamber 200 can be configured to separate a stream (e.g., polymerization product stream 120 comprising polyethylene) into gases, liquids, solids, or combinations thereof.

In an embodiment, the separator for separating the polymerization product stream into a polymer stream and a gas stream can comprise a vapor-liquid separator. As will be appreciated by one of skill in the art, and with the help of this disclosure, the solids of the polymerization product stream (e.g., polymer fluff) are slurried in the liquids of the polymerization product stream, and a vapor-liquid separator would generally separate the solids and the liquid in a single slurry phase from the gases of the polymerization product stream. Nonlimiting examples of separators suitable for use in the present disclosure a fixed-bed adsorption column, a flash tank, a filter, a membrane, a reactor, an absorbent, an adsorbent, a molecular sieve, or combinations thereof.

In an embodiment, the separator comprises a flash tank (e.g., flash chamber 200). Without wishing to be limited by theory, such a flash tank can comprise a vessel configured to vaporize and/or remove low vapor pressure components from a high temperature and/or high pressure fluid. The separator for separating the polymerization product into a polymer stream and a gas stream can be configured such that an incoming stream can be separated into a liquid stream (e.g., a condensate stream) and a gas (e.g., vapor) stream. The liquid stream can comprise a reaction product (e.g., polyethylene, often referred to as "polymer fluff"). The liquid stream can be a bottoms stream. The gas or vapor stream can comprise volatile solvents, gaseous, unreacted monomers and/or optional comonomers, waste gases (secondary reaction products, such as contaminants and the like), or combinations thereof. The gas stream can be an overhead stream.

The separator for separating the polymerization product into a polymer stream and a gas stream can be configured such that the polymerization product stream is flashed by heat, pressure reduction, or both such that an enthalpy of the polymerization product stream is increased. This can be accomplished via a heater, a flashline heater, various other operations commonly known in the art, or combinations thereof. For example, a flash line heater comprising a double pipe can exchange heat by hot water or steam. Such a flashline heater can increase the temperature of the stream while reducing its pressure.

In one or more embodiments, separating the polymerization product stream into a polymer stream and a gas stream can comprise distilling, vaporizing, flashing, filtering, membrane screening, centrifuging, absorbing, adsorbing, or combinations thereof, the polymerization product. In the embodiments illustrated in FIG. 1A and/or FIG. 1B, separating the polymerization product stream into a polymer stream and a gas stream yields a gas stream 210 and a polymer stream 220 (e.g., polyethylene polymer, copolymer, etc.).

In an embodiment, the gas stream 210 can comprise unreacted monomer (e.g., unreacted ethylene monomer), optional unreacted comonomer, and various gases. Gas stream 210 can comprise the non-solid components of polymerization product stream 120 in a vapor phase. In an embodiment, the gas stream 210 can comprise hydrogen, nitrogen, methane, ethylene, ethane, propylene, propane, butane, isobutane, pentane, hexane, 1-hexene, heavier hydrocarbons, or combinations thereof. In an embodiment, the gas stream 210 can further comprise trace amounts of oxygen. In an embodiment, ethylene can be present in a range of from about 0.1% to about 15%, alternatively, from about 1.5% to about 5%, alternatively, about 2% to about 4% by total weight of the gas stream. Ethane can be present in a range of from about 0.001% to about 4%, alternatively, from about 0.2% to about 0.5% by total weight of the gas stream. Isobutane can be present in a range from about 80% to about 98%, alternatively, from about 92% to about 96%, alternatively, about 95% by total weight of the gas stream.

In some embodiments, the mid-polymerization reactor stream 15 can be processed in a similar manner to the polymerization product stream 121, wherein the mid-polymerization reactor stream 15 can be separated into a mid-polymerization polymer stream and a mid-polymerization gas stream. In such embodiments, the mid-polymerization polymer stream can be communicated to the second reactor 106; processed in a similar manner to the polymer stream 220, as will be described in more detail later herein; communicated to the purge column 400, such as for example via the polymer stream 220; or combinations thereof. In such embodiments, the mid-polymerization gas stream can be processed in a similar manner to the gas stream 210, as will be described in more detail later herein, and/or communicated to the heavy distillation column 300 and/or to the distillation column 301, such as for example via the gas stream 210.

In an embodiment, the PEP process 2000 can generally comprise the step 2400 of purging the polymer stream to produce a purged polymer stream and a spent purge gas stream. In the embodiment of the PEP system 1000 shown in FIG. 1A and/or the embodiment of the PEP system 1001 shown in FIG. 1B, a primary solids feed to the purge column 400 comprises typically the polymer stream 220. Generally, the polymer stream 220 comprises a solids discharge (e.g., polyolefin fluff, such as for example polyethylene fluff) that exits the flash chamber 200. A purpose of the purge column 400 is to remove residual hydrocarbon from polymer stream 220 and to provide a substantially-clean polymer fluff (e.g., polymer 425) with relatively small amounts of entrained volatile organic content. The polymer 425 (e.g., polymer fluff) can be transported or conveyed to an extrusion/loadout system for conversion to pellets and/or for distribution and sale as polyolefin pellet resin.

Referring to the embodiments of FIG. 1A and/or FIG. 1B, the polymer stream 220 can comprise a polymer (e.g., polyethylene), unreacted monomer (e.g., ethylene, 1-hexene) and various gases (e.g., ethane, isobutane, hydrogen, methane, propane, butane, pentane, hexane, propylene). Processing (e.g., purging) the polymer stream 220 can yield the purged polymer stream 420 and the spent purge gas stream 430 generally comprising a purge gas (e.g., nitrogen), unreacted monomer (e.g., ethylene, 1-hexene), and various gases (e.g., ethane, isobutane, hydrogen, nitrogen, methane, propylene, propane, butane, pentane, hexane, heavier hydrocarbons).

Referring to the embodiments of FIG. 1A and/or FIG. 1B, a purge gas 410 (e.g., an inert gas, nitrogen) can be circulated through purge column 400 to remove residual hydrocarbons via a spent purge gas stream 430. In some embodiments, the spent purge gas stream 430 can be communicated to a separation unit, such as for example an INRU unit, for hydrocarbon separation and/or recovery.

In an embodiment, purge column 400 can be a cylindrical vessel having a relatively tall vertical section, a cover or head at the top, sloped sides or conical shape at the bottom with an opening for polymer fluff discharge. The polymer fluff to be degassed of volatile hydrocarbons can enter the vessel at the top, while the purge gas, typically nitrogen, can be introduced to the vessel in the sloped bottom sides. Flow can be countercurrent between the purge gas and polymer fluff in the vessel. In certain embodiments, a hydrocarbon rich purge gas (e.g., spent purge gas 430) can leave the purge column through an opening at the top, while a degassed fluff (e.g., purged polymer stream 420) can leave at the bottom of the purge column.

Degassing effectiveness in the purge column can be predicated on the maintenance of an uniform plug flow of the polymer fluff and purge gas in the purge column, thereby ensuring good contact between the two. A diameter (D) of the purge column can typically range from about 5 to about 6 feet, but a length (L) of the purge column can be chosen to achieve a residence time (e.g., from about 30 to about 180 minutes) sufficient for degassing the polymer fluff. In some embodiments, L/D ratios can range from about 4 to about 8; however, L/D ratios can be outside this range. In an embodiment, internal features can be employed in the purge column, such as a distributor plate for introducing purge gas (e.g., nitrogen), an inverted cone for facilitating plug flow of the polymer (e.g., to reduce bridging or channeling of the polymer fluff), and the like.

In one or more of the embodiments disclosed herein, processing the purged polymer stream 420 (e.g., polymer 425) comprises any suitable process or series of processes configured to produce a polymer product as can be suitable for commercial or industrial usage, storage, transportation, further processing, or combinations thereof.

In an embodiment, processing the purged polymer stream 420 can comprise routing the purged polymer stream 420 to a polymer processor. The polymer processor can be configured for the performance of a suitable processing means (e.g., to form various articles), nonlimiting examples of which include cooling, injection molding, melting, pelletizing, film blowing, cast film, blow molding, extrusion molding, rotational molding, thermoforming, cast molding, fiber spinning, and the like, or combinations thereof. Various additives and modifiers can be added to the polymer to provide better processing during manufacturing and for desired properties in the end product. Nonlimiting examples of such additives can include surface modifiers such as slip agents, antiblocks, tackifiers; antioxidants such as primary and secondary antioxidants; pigments; processing aids such as waxes/oils and fluoroelastomers; and/or special additives such as fire retardants, antistats, scavengers, absorbers, odor enhancers, and degradation agents.

The polymer can include other suitable additives. Such additives can be used singularly or in combination and can be included in the polymer before, during or after preparation of the polymer as described herein. Such additives can be added via known techniques, for example during an extrusion or compounding step such as during pelletization or subsequent processing into an end use article.

In an embodiment, the polymer processor can be configured to form a suitable polymer product. Nonlimiting examples of suitable polymer products as can result from processing the purged polymer stream include films, powders, pellets, resins, liquids, or any other suitable form as will be appreciated by those of skill in the art. Such a suitable output can be for use in, for example, one or more of various consumer or industrial products. For example, the polymer product can be utilized in any one or more of various articles, including, but not limited to, bottles, drums, toys, containers, household containers, utensils, film products, tanks, fuel tanks, pipes, membranes, geomembranes, and liners. In an embodiment, the polymer processor is configured to form pellets for transportation to a consumer product manufacturer.

In an embodiment, the PEP process 2000 can generally comprise the step 2500 of processing the gas stream in one or more distillation columns to produce a light hydrocarbon stream. In an embodiment, processing the gas stream 210 can comprise separating at least one gaseous component from the gas stream. While the step of processing the gas stream will be discussed in detail in the context of two distillation columns used for such processing of the gas stream, it should be understood that any suitable number of distillation columns can be used for processing the gas stream, such as for example one, two, three, four, five, or more distillation columns.

In an embodiment, separating at least one gaseous component from the gas stream can comprise distilling a gas stream (e.g., gas stream 210) in one step so as to allow at least one gaseous component to separate from other gaseous components according to temperature(s) of boiling. In the embodiment of the PEP system 1001 shown in FIG. 1B, distillation column 301 can be configured to separate at least one gaseous component from a gas stream (e.g., gas stream 210). The gas stream 210 can be communicated to the distillation column 301. Gas stream 210 can be distilled in the distillation column 301 to form light hydrocarbon stream 304, distillation bottoms stream 302, and distillation side stream 303. The light hydrocarbon stream 304 can comprise ethylene, ethane, optionally hydrogen, or combinations thereof. The light hydrocarbon stream 304 can be communicated to the PSA unit 500. The distillation bottoms stream 302 can comprise hexane, hexene, optionally isobutane, or combinations thereof. The distillation side stream 303 can comprise isobutane.

In the embodiment of the PEP system 1000 shown in FIG. 1A, distillation columns 300 and 350 can be configured to separate at least one gaseous component from a gas stream (e.g., gas stream 210). Processing the gas stream 210 in one or more distillation columns can yield several hydrocarbon fractions. The gas stream 210 can be communicated to the heavy distillation column 300. Gas stream 210 can be distilled in the heavy distillation column 300 to form intermediate hydrocarbon stream 330 which can be communicated to the light distillation column 350. Non-distilled components in the heavy distillation column 300 can emit from the heavy distillation column 300 in heavy distillation bottoms stream 310. Heavy distillation side stream 320 can optionally emit from the heavy distillation column 300.

Intermediate hydrocarbon stream 330 can be characterized as comprising, alternatively, comprising substantially, alternatively, consisting essentially of, alternatively, consisting of, $C_4$ and lighter hydrocarbons (e.g., butane, isobutane, propane, propylene, ethane, ethylene, methane, etc.) and any light gases (e.g., nitrogen). For example, $C_4$ and lighter hydrocarbons and gases can be present in the intermediate hydrocarbon stream 330 in an amount of from about 80% to about 100% by total weight of the intermediate hydrocarbon stream, alternatively from about 90% to about 99.999999%, alternatively from about 99% to about 99.9999%, alternatively, $C_5$ and heavier hydrocarbons can be present in the intermediate hydrocarbon stream 330 in an amount from about 0% to about 20% by total weight of the intermediate hydrocarbon stream, alternatively from about 10% to about 0.000001%, alternatively from about 1.0% to about 0.0001%. Also, for example, at least 90% by weight of the $C_4$ and lighter hydrocarbons and gases of the gas stream 210 can be present in the intermediate hydrocarbon stream 330, alternatively, at least 98%, alternatively, at least 99%.

In an embodiment, heavy distillation bottoms stream 310 can be characterized as comprising $C_6$ and heavy components (e.g., $C_6$ and heavier alkanes and oligomers), wherein the heavy components can comprise alkanes, that is, alkanes larger than hexane (e.g., heptane and/or other large alkanes). In an embodiment, hydrocarbons other than $C_6$ and heavy alkanes (e.g., $C_6$ and heavier alkanes and oligomers) can be present in the heavy distillation bottoms stream 310 in an amount less than about 15%, alternatively, less than about 10%, alternatively, less than about 5% by total weight of the heavy distillation bottoms stream 310. In an embodiment, the heavy distillation bottoms stream 310 can be directed to additional processing steps or methods, or alternatively they can be disposed of, as appropriate. In an embodiment, heavy distillation bottoms stream 310 can be incinerated.

In an embodiment, heavy distillation side stream 320 can be characterized as comprising hexene. For example, hexene can be present in heavy distillation side stream 320 in an amount of from about 20% to about 98% by total weight of the heavy distillation side stream 320, alternatively from about 40% to about 95%, alternatively from about 50% to about 95%.

In an embodiment, the heavy distillation side stream 320 can be recycled. In an embodiment, recycling the heavy distillation side stream 320 can comprise routing, for example, via a suitable pump or compressor, the heavy distillation side stream 320 back to and/or introducing the heavy distillation side stream 320 into one or more components of the PEP system 1000, for example, into slurry loop reactor system 100 for reuse in a polymerization reaction. Recycling the heavy distillation side stream 320 can provide an efficient and/or cost-effective means of supplying hexene for operation of the polymerization reaction process. In an embodiment, at least a portion of the hexene of the heavy distillation side stream 320 can be employed in the polymerization reaction as, for example, a comonomer in the reaction. In an alternative embodiment, at least a portion of the heavy distillation side stream 320 can be routed to storage for subsequent use in a polymerization reaction or employed in any other suitable process. As will be appreciated by one of skill in the art, and with the help of this disclosure, at least a portion of the hexene can be recycled back to the reactor when the reactor is undergoing a polymerization reaction involving hexene as a comonomer. Further, as will be appreciated by one of skill in the art, and with the help of this disclosure, at least a portion of the hexene can be stored when the reactor is undergoing a polymerization reaction in the absence of hexene.

In some embodiments, at least a portion of the heavy distillation bottoms stream 310 and/or heavy distillation side stream 320 can be returned to the heavy distillation column 300. For example, at least a portion of the heavy distillation bottoms stream 310 and/or heavy distillation side stream 320 can be routed via a reboiler to the heavy distillation column 300 for additional processing.

In an embodiment, heavy distillation column 300 can be provided with one or more inlets and at least two outlets. The heavy distillation column 300 can be operated at a suitable temperature and pressure, for example as can be suitable to achieve separation of the components of the gas stream 210. For example, the heavy distillation column 300 can be operated at a temperature in a range of from about 15° C. to about 233° C., alternatively, from about 20° C. to about 200° C., alternatively, from about 20° C. to about 180° C., and/or a pressure in a range of from about 14.7 psi to about 527.9 psi, alternatively, from about 15.7 psi to about 348 psi, alternatively, from about 85 psi to about 290 psi. The heavy distillation column 300 can be configured and/or sized to provide for separation of a suitable volume of gases (e.g., a flash gas stream). As will be appreciated by one of skill in the art viewing this disclosure, the gas stream 210 can remain and/or reside within heavy distillation column 300 for any suitable amount of time, for example an amount of time as can be necessary to provide sufficient separation of the components within the heavy distillation column 300.

In an embodiment, the gas stream 210 can be introduced into the heavy distillation column 300 without a compressive step, that is, without compression of the gas stream 210 after it is emitted from the flash chamber 200 and before it is introduced into the heavy distillation column 300. In another embodiment, the gas stream 210 can be introduced into the heavy distillation column 300 at substantially the same pressure as the outlet pressure of flash chamber 200 (e.g., a pressure of from about 14.7 psia to about 527.9 psia, alternatively, from about 15.7 psia to about 348 psia, alternatively, from about 85 psia to about 290 psia at the outlet of the flash chamber 200). In still another embodiment, the gas stream 210 can be introduced into the heavy distillation column 300 without a significant compressive step. In some embodiments, a compressor (e.g., a flash compressor) can be used to raise the pressure of the gas stream 210 to a required level for introducing into heavy distillation column 300. In other embodiments, gas stream 210 can be introduced into heavy distillation column 300 at a pressure in a range of from about 25 psi less than the pressure at which the gas stream 210 was emitted from the flash chamber 200 to about 25 psi greater than the pressure at which the gas stream 210 was emitted from the flash chamber 200, alternatively, from about 15 psi less than the pressure at which the gas stream 210 was emitted from the flash chamber 200 to about 15 psi greater than the pressure at which the gas stream 210 was emitted from the flash chamber 200, alternatively, from about 5 psi less than the pressure at which the gas stream 210 was emitted from the flash chamber 200 to about 5 psi greater than the pressure at which the gas stream 210 was emitted from the flash chamber 200. In an embodiment, the gas stream 210 can be introduced into the heavy distillation column 300 at a pressure in a range of from about 14.7 psia to about 527.8 psia, alternatively, from about 15.7 psia to about 348 psia, from about 85 psia to about 290 psia.

In an embodiment, the heavy distillation column 300 can be configured and/or operated such that each of the intermediate hydrocarbon stream 330, the heavy distillation bottoms stream 310, and an optional heavy distillation side stream 320 can comprise a desired portion, part, or subset of components of the gas stream 210. For example, as will be appreciated by one of skill in the art and with the help of this disclosure, the location of a particular stream outlet, the operating parameters of the heavy distillation column 300, the composition of the gas stream 210, or combinations thereof can be manipulated such that a given stream can comprise a particular one or more components of the gas stream 210.

In the embodiment of the PEP system 1000 shown in FIG. 1A, the intermediate hydrocarbon stream 330 can be separated in the light distillation column 350 to form light hydrocarbon stream 380, light distillation bottoms stream 360, and optionally, light distillation side stream 370. At least one gaseous component can be emitted from the light distillation column 350 in light hydrocarbon stream 380, and the other gaseous components can be emitted from the light distillation column 350 in light distillation bottoms stream 360.

In an embodiment, light hydrocarbon stream 380 can be characterized as comprising ethylene and ethane. For example, ethylene can be present in light hydrocarbon stream 380 in an amount from about 30% to about 99% by total weight of the light hydrocarbon stream 380, alternatively from about 40% to about 98%, alternatively from about 60% to about 98%, alternatively from about 50% to about 95%, alternatively from about 70% to about 95%, or alternatively from about 70% to about 90%. Further, for example, ethane can be present in light hydrocarbon stream 380 in an amount from about 1% to about 70% by total weight of the light hydrocarbon stream 380, alternatively from about 2% to about 60%, alternatively from about 2% to about 40%, alternatively from about 5% to about 50%, alternatively from about 5% to about 30%, or alternatively from about 10% to about 30%.

In an embodiment, the light hydrocarbon stream 380 can further comprise other light gases (e.g., methane, carbon dioxide, nitrogen, hydrogen, or combinations thereof).

In an embodiment, light distillation bottoms stream 360 can be characterized as comprising propane, butane, isobutane, pentane, hexane, heavier saturated hydrocarbons, or combinations thereof. In an embodiment, the light distillation bottoms stream 360 can be free of olefins, alternatively, substantially free of olefins, alternatively, essentially free of olefins, alternatively, consisting essentially of or consisting of non-olefins. For example, olefins can be present in light distillation bottoms stream 360 in an amount of less than about 1.0% by total weight of the light distillation bottoms stream 360, alternatively, less than about 0.5%, alternatively, less than about 0.1%. In an embodiment, the light distillation bottoms stream 360 can comprise olefin-free isobutane 365.

In an embodiment, light distillation side stream 370 can be characterized as comprising isobutane. In an embodiment, light distillation side stream 370 comprising, alternatively, consisting of or essentially consisting of, isobutane can be emitted from the light distillation column 350. The isobutane of light distillation bottoms stream 360 can comprise a different grade of isobutane than the isobutane of light distillation side stream 370. For example, light distillation bottoms stream 360 can comprise isobutane that is substantially free of olefins, and light distillation side stream 370 can comprise a recycle isobutane which can include olefins.

In an embodiment, at least a portion of the light distillation side stream 370 and/or light distillation bottoms stream 360 can be recycled. In some embodiments, recycling at least a portion of the light distillation side stream 370 and/or light distillation bottoms stream 360 can comprise routing, for example, via a suitable pump or compressor, at least a portion of the light distillation side stream 370 and/or light distillation bottoms stream 360 back to and/or introducing at least a portion of the light distillation side stream 370 and/or light distillation bottoms stream 360 into one or more components of the PEP system 1000, for example, into slurry loop reactor system 100 for reuse in a polymerization reaction. In an embodiment, at least a portion of the light distillation side stream 370 and/or light distillation bottoms stream 360 can be combined with various other components (catalysts, cocatalysts, etc.) to form a catalyst slurry that can be introduced into one or more of reactors 104, 106. Without wishing to be limited by theory, because at least a portion of light distillation bottoms stream 360 can be free of olefins and can comprise isobutane, the light distillation bottoms stream 360 can be mixed with catalytic components (e.g., catalysts, cocatalysts, etc.) without the risk of unintended polymerization reactions (e.g., polymerization prior to introduction into the one or more reactors). As such, at least a portion of light distillation bottoms stream 360 can serve as a source of olefin-free isobutane for a polymerization reaction. Recycling at least a portion of the light distillation side stream 370 and/or light distillation bottoms stream 360 can provide an efficient and/or cost-effective means of supplying isobutane for operation of the polymerization reaction process. In an alternative embodiment, at least a portion of the light distillation side stream 370 and/or light distillation bottoms stream 360 can be routed to storage for subsequent use in a polymerization reaction or employed in any other suitable process.

In some embodiments, at least a portion of the light distillation bottoms stream 360 can be recycled to a PSA unit, for example via a sweeping gas stream (e.g., sweeping gas stream 510). The light distillation bottoms stream 360 comprising olefin-free isobutane 365 can be recycled 366 to the PSA unit 500, for example via the sweeping gas stream 510, as shown in FIG. 1A and/or FIG. 1B.

In other embodiments, at least a portion of the light distillation side stream 370 and/or light distillation bottoms stream 360 can be routed to storage for subsequent use in any suitable process.

In yet other embodiments, at least a portion of the light distillation side stream 370 and/or light distillation bottoms stream 360 can be returned to the light distillation column 350. For example, at least a portion of the light distillation side stream 370 and/or light distillation bottoms stream 360 can be routed via a reboiler to the light distillation column 350 for additional processing.

The light distillation column 350 can be configured and/or sized to provide for separation of a suitable volume of gases. For example, the light distillation column 350 can be operated at a temperature in a range of from about 50° C. to about −35° C., alternatively, from about 50° C. to about −30° C., alternatively, from about 50° C. to about −20° C., alternatively, from about 50° C. to about −10° C., alternatively, from about 50° C. to about 0° C., alternatively, from about 50° C. to about 10° C., alternatively, from about 50° C. to about 20° C., alternatively, from about 40° C. to about 10° C., alternatively, from about 30° C. to about 5° C., and a pressure in a range of from about 14.7 psia to about 529.7 psia, alternatively, from about 15.7 psia to about 348 psia, alternatively, from about 85 psia to about 290 psia. The light distillation column 350 can be configured and/or sized to provide for separation of a suitable volume of intermediate hydrocarbon stream 330. As will be appreciated by one of skill in the art, the intermediate hydrocarbon stream 330 can remain and/or reside within light distillation column 350 for any suitable amount of time as can be necessary to provide sufficient separation of the components of intermediate hydrocarbon stream 330. In an embodiment, light distillation column 350 can be provided with at least two outlets.

In an embodiment, the light distillation column 350 can be configured and/or operated such that each of light hydrocarbon stream 380 and the light distillation bottoms stream 360 can comprise a desired portion, part, or subset of components of the intermediate hydrocarbon stream 330. For example, as will be appreciated by one of skill in the art with the aid of this disclosure, the location of a particular stream inlet or outlet, the operating parameters of the light distillation column 350, the composition of the intermediate hydrocarbon stream 330, or combinations thereof can be manipulated such that a given stream can comprise a particular one or more components of the intermediate hydrocarbon stream 330.

In an embodiment, the PEP process 2000 can generally comprise the step 2600 of contacting the light hydrocarbon stream with a purged hydrocarbon adsorber to yield a loaded hydrocarbon adsorber and a non-adsorbed gas stream. In an embodiment, at least one gaseous component (e.g., ethylene) can be separated from the light hydrocarbon stream 380 during step 2600.

In one or more one or more of the embodiments disclosed herein, separating at least one gaseous component from a gas stream (e.g., light hydrocarbon stream 380, light hydrocarbon stream 304, etc.) generally comprises any suitable method of selectively separating at least a first chemical component or compound from a stream comprising the first chemical component or compound and one or more other chemical components, compounds, or the like. In various embodiments, the gaseous component separated from the gas stream can comprise one or more hydrocarbons. Non-limiting examples of such hydrocarbons include alkanes (e.g., ethane, butane, isobutane, hexane, and the like, or combinations thereof) and alkenes or olefin monomers (e.g., ethylene) or optional comonomers. In an embodiment, the gaseous component separated from the gas stream can comprise an unreacted hydrocarbon monomer, e.g., ethylene. Optionally, the gaseous component separated from the gas stream can comprise an unreacted hydrocarbon comonomer. In an embodiment, the gaseous component separated from the gas stream can comprise an unreacted hydrocarbon monomer (e.g., ethylene, alone or in combination with other hydrocarbons, such as, ethane, isobutane, hexane, or combinations thereof), or optionally, hydrocarbon comonomer alone or in combination with other hydrocarbons, such as, ethane, isobutane, hexane, or combinations thereof. In an embodiment, the gaseous component separated from the gas stream can comprise ethane. Nonlimiting examples of suitable separating means include distilling, vaporizing, flashing, filtering, membrane screening, absorbing, adsorbing, molecular weight exclusion, size exclusion, polarity-based separation, and the like, or combinations thereof.

In an embodiment, at least one gaseous component (e.g., ethane) can be separated from the light hydrocarbon stream 380 and/or light hydrocarbon stream 304 by pressure swing adsorption (PSA), thereby enabling ethylene recovery, as will be described in more detail herein. As will be appreciated by one of skill in the art, and with the help of this disclosure, separating ethane from a gas stream (e.g., light hydrocarbon stream 380, light hydrocarbon stream 304, etc.) by adsorbing ethane in a PSA unit enables the recovery of ethylene as recovered or non-adsorbed ethylene, such as for example as part of a non-adsorbed gas stream.

Recovering ethylene from the light hydrocarbon stream 380 and/or 304 can generally comprise contacting the light hydrocarbon stream 380 and/or 304 with a purged hydrocarbon adsorber in a PSA unit 500 to yield a loaded hydrocarbon adsorber generally comprising adsorbed ethane, and a non-adsorbed gas stream 520 generally comprising ethylene (e.g., recovered or non-adsorbed ethylene). In an embodiment, the non-adsorbed gas stream 520 can further comprise other light gases (e.g., methane, carbon dioxide, nitrogen, hydrogen, or combinations thereof) that were present in the light hydrocarbon stream 380 and/or 304. In embodiments where a sweeping gas is introduced to the PSA unit 500 during step 2600 of contacting the light hydrocarbon stream with a purged hydrocarbon adsorber, the non-adsorbed gas stream 520 can generally comprise ethylene, isobutane, and nitrogen; alternatively ethylene and isobutane; or alternatively ethylene and nitrogen.

For purposes of the disclosure herein, the term "loaded" when used to describe or when referring to a hydrocarbon adsorber (e.g., "loaded hydrocarbon adsorber"), is intended to be nonlimiting, and is intended to denote (e.g., mean, signify, indicate, represent, etc.) that the hydrocarbon adsorber has an amount of a hydrocarbon (e.g., ethane) adsorbed therein (e.g., adsorbed ethane). Further, for purposes of the disclosure herein, the term "loaded" when used to describe a hydrocarbon adsorber (e.g., "loaded hydrocarbon adsorber"), is intended to include any amount of an adsorbed hydrocarbon, such as for example an amount of adsorbed hydrocarbon of equal to or greater than about 10%, alternatively equal to or greater than about 15%, alternatively equal to or greater than about 20%, alternatively equal to or greater than about 25%, alternatively equal to or greater than about 30%, alternatively equal to or greater than about 40%, alternatively equal to or greater than about 50%, alternatively equal to or greater than about 60%, alternatively equal to or greater than about 70%, alternatively equal to or greater than about 80%, alternatively equal to or greater than about 90%, alternatively equal to about 100%, based on adsorption capacity of the hydrocarbon adsorber at a given pressure (e.g., first pressure). Without wishing to be limited by theory, the adsorption capacity of the hydrocarbon adsorber at a given pressure (e.g., first pressure) can be defined as the ratio of the maximum amount of hydrocarbon that can be adsorbed by the hydrocarbon adsorber to the amount of hydrocarbon adsorber present in the PSA unit, and it can be expressed in g adsorbed hydrocarbon/g hydrocarbon adsorber. As will be appreciated by one of skill in the art and with the help of this disclosure, the term "adsorbed hydrocarbon" refers to a hydrocarbon (e.g., ethane) that is adsorbed or associated with an adsorbent (e.g., adsorbent associated hydrocarbon) in a reversible fashion, wherein the adsorbent is a hydrocarbon adsorber of the type disclosed herein.

In an embodiment, the loaded hydrocarbon adsorber can be a partially loaded hydrocarbon adsorber, wherein the partially loaded hydrocarbon adsorber can comprise an amount of adsorbed hydrocarbon of from about 10% to about 50%, alternatively from about 15% to about 45%, or alternatively from about 20% to about 40%, based on the adsorption capacity of the hydrocarbon adsorber at the first pressure.

In an embodiment, the loaded hydrocarbon adsorber can be a substantially loaded hydrocarbon adsorber, wherein the substantially loaded hydrocarbon adsorber can comprise an amount of adsorbed hydrocarbon of from about 50% to about 99%, alternatively from about 55% to about 95%, or alternatively from about 60% to about 90%, based on the adsorption capacity of the hydrocarbon adsorber at the first pressure.

In an embodiment, the loaded hydrocarbon adsorber can be a completely or fully loaded hydrocarbon adsorber (alternatively referred to as a saturated hydrocarbon adsorber), wherein the completely loaded hydrocarbon adsorber can comprise an amount of adsorbed hydrocarbon of about 100%, alternatively about 99.5%, or alternatively about 99%, based on the adsorption capacity of the hydrocarbon adsorber at the first pressure.

As will be appreciated by one of skill in the art, and with the help of this disclosure, the hydrocarbon adsorber can undergo an adsorption step (e.g., the hydrocarbon adsorber can adsorb or load a compound) to yield a loaded hydrocarbon adsorber, such as for example a substantially loaded hydrocarbon adsorber or a completely loaded hydrocarbon adsorber, and subsequently the loaded hydrocarbon adsorber (e.g., substantially loaded hydrocarbon adsorber, completely loaded hydrocarbon adsorber) can undergo a desorption step (e.g., the hydrocarbon adsorber can desorb or unload a compound) to yield an unloaded hydrocarbon adsorber or a partially loaded hydrocarbon adsorber. The hydrocarbon adsorber can be characterized by a first adsorption capacity at the first pressure, and by a second adsorption capacity at a second pressure, wherein the first pressure is greater than the second pressure, and wherein the first adsorption capacity is greater than the second adsorption capacity, thereby enabling an adsorption or loading step at the first pressure and a desorption or unloading step at the second pressure.

In an embodiment, separating at least one gaseous component from the light hydrocarbon stream can comprise contacting the light hydrocarbon stream with an adsorbent (e.g., hydrocarbon adsorber, purged hydrocarbon adsorber as disclosed herein), for example, so as to allow the gaseous component to be adsorbed by the adsorbent. In such an embodiment, separating at least one gaseous component from the light hydrocarbon stream comprises selectively adsorbing the at least one gaseous component from a light hydrocarbon stream. In such an embodiment, adsorbing the at least one gaseous component from the light hydrocarbon stream generally comprises contacting the light hydrocarbon stream with a suitable adsorbent, allowing the at least one component to be adsorbed by the adsorbent, and, recovering a stream comprising unadsorbed gases (e.g., non-adsorbed gas stream 520), such as for example recovered or non-adsorbed ethylene. In an additional embodiment, separating at least one gaseous component from the light hydrocarbon stream can further comprise liberating the adsorbed gaseous component from the adsorbent (e.g., recovered adsorbed gas stream 530), such as for example liberating ethane.

In an embodiment, the hydrocarbon adsorber comprises a substance, material and/or compound capable of facilitating adsorption and desorption of a hydrocarbon (e.g., ethane) from a hydrocarbon mixture (e.g., light hydrocarbon stream) by way of a pressure swing adsorption process. For example, the hydrocarbon adsorber can comprise a substance, material and/or compound capable of adsorbing hydrocarbons, preferably in a selective manner. Generally, the hydrocarbon adsorber can comprises any material capable of selectively adsorbing one or more hydrocarbon components of a gas mixture (e.g., a light hydrocarbon stream). In an embodiment, the hydrocarbon adsorber can selectively adsorb one or more hydrocarbons at a first pressure, and can selectively desorb (e.g., regenerate, unload) one or more hydrocarbons at a second pressure, wherein the first pressure is greater than the second pressure.

In an embodiment, the hydrocarbon adsorber comprises a zeolitic imidazolate framework (ZIF). Generally, ZIFs are a subclass or subfamily of metal organic frameworks (MOFs), wherein the ZIFs display exceptional thermal stability. Generally, ZIFs comprise tetrahedrally-coordinated metal ions connected by organic imidazole linkers. ZIFs are named for the resemblance of their metal-imidazolate-metal bond angles to Si—O—Si angles in zeolites. ZIFs are generally thought to combine the high stability of inorganic zeolites with the high porosity and organic functionality of MOFs. Because of their stability, wide topological variety, and intrinsic hydrophobic properties, ZIFs are very attractive for many separation applications. For purposes of the disclosure herein, ZIFs are defined as microporous crystalline structures having framework topologies commonly found in zeolites and/or in other crystalline materials wherein each vertex of a framework structure is comprised of a single metal ion and each pair of connected adjacent vertices of the framework structure is linked by nitrogen atoms of an imidazolate anion or a derivative of an imidazolate anion. Generally, the ZIF framework structure defines ZIF cages/cavities/pores. Further, for purposes of the disclosure herein, the term "microporous" when used to describe or when referring to a ZIF is defined as having a pore window size of less than about 2.0 nm or 20 Angstroms. For purposes of the disclosure herein, a pore window of a ZIF refers to an opening or "window" that diffusing molecules have to pass through in order to diffuse from one ZIF cage/cavity/pore to an adjacent ZIF cage. Further, for purposes of the disclosure herein, a pore window size of a ZIF is a geometric parameter that refers to the diameter of the window that connects adjacent ZIF cages that allows the passage of diffusing molecules from one ZIF cage to an adjacent ZIF cage. ZIFs and their use in separation processes are described in more detail in U.S. Pat. No. 8,192,709; *J. Am. Chem. Soc.* 2010, 132, pp 17704-17706; *Microporous and Mesoporous Materials* 2012, 147, pp 135-141; and *Langmuir* 2013, 29, pp 8592-8600; each of which is incorporated by reference herein in its entirety.

Nonlimiting examples of metals suitable for use in the present disclosure as part of ZIF structures include Zn, Co, Ni, Fe, Cu, Mg, and the like, or combinations thereof.

Nonlimiting examples of ZIFs suitable for use as hydrocarbon adsorbers in the present disclosure include ZIF-7, ZIF-8, ZIF-65, ZIF-67, or combinations thereof.

In an embodiment, the ZIF can be characterized by a pore window size of from about 0.2 nm to about 0.5 nm, alternatively from about 0.25 nm to about 0.45 nm, or alternatively from about 0.3 nm to about 0.4 nm.

Generally, ZIF materials can be regarded as having a certain degree of framework flexibility. ZIF cages are interconnected and comprise windows to allow hydrocarbons to enter the ZIF cages and be adsorbed in such cages. In some embodiments, the pore window size can be such that only certain hydrocarbons will be able to enter through the window and be adsorbed within the cages. Without wishing to be limited by theory, certain ZIFs can exhibit a gate-opening effect upon exposure to a hydrocarbon mixture, such as for example an ethane/ethylene mixture, leading to the selective hydrocarbon (e.g., ethane) adsorption on certain ZIFs. A more detailed description of ZIFs, their structure, synthesis and properties can be found in U.S. Pat. No. 8,314,245, which is incorporated by reference herein in its entirety.

In an embodiment, the hydrocarbon adsorber suitable for use in the present disclosure comprises particles (e.g., hydrocarbon adsorber particles, ZIF particles) of any suitable geometry, including without limitation particles, pellets, beads, hollow beads, spheres, ovals, fibers, hollow fibers, tubes, hollow tubes, rods, platelets, disks, plates, ribbons, and the like, or combinations thereof. In an embodiment, the hydrocarbon adsorber can be characterized by a particle size of from about 0.1 mm to about 5 mm, alternatively from about 0.2 mm to about 2.5 mm, or alternatively from about 0.25 mm to about 1 mm.

In an embodiment, the hydrocarbon adsorber further comprises a support, wherein the ZIF contacts at least a portion of the support, is distributed throughout the support, or combinations thereof, and whereby the ZIF is structurally supported by the support. In an embodiment, the ZIF can be disposed about the support. In an embodiment, the ZIF can be associated with the support.

The support can be comprised of any suitable material and/or of any suitable construction and can be porous or non-porous. In some embodiments, the support can be comprised entirely of a ZIF. In other embodiments, the support can be comprised entirely of a (relatively) non-adsorbent material towards hydrocarbons.

In an embodiment, the support has a porosity of from about 0 vol. % to about 99 vol. %, alternatively from about 1 vol. % to about 90 vol. %, or alternatively from about 10 vol. % to about 75 vol. %, based on the total volume of the support. As will be appreciated by one of skill in the art, and with the help of this disclosure, the support has an open cell pore structure, such that ZIFs could be deposited inside the pores of the support, thereby providing a larger surface area for hydrocarbon adsorption. Generally an open cell structure refers to a structure characterized by a high porosity, low density material typically containing pores that are connected to each other. As will be appreciated by one of skill in the art, and with the help of this disclosure, a support open cell structure also enables the unhindered flow of gaseous mixtures (e.g., hydrocarbon mixtures, light hydrocarbon stream, etc.) through the support, and as such the gaseous mixture may efficiently contact the ZIFs. As will be appreciated by one of skill in the art, and with the help of this disclosure, the support could provide certain properties that could facilitate the pressure swing adsorption process, such as for example enhanced (e.g., faster) heat transfer. Further, as will be appreciated by one of skill in the art, and with the help of this disclosure, the support could also provide for an enhanced surface area.

In an embodiment, the support can contact a ZIF, wherein the ZIF comprises a layer or coating on the support; wherein the ZIF can be embedded within the structure of the support; and the like; or combinations thereof. In an embodiment, the support comprises a support outer surface, wherein at least a portion of the support outer surface can be in contact with the ZIF.

In an embodiment, the ZIF can form a ZIF layer contacting the support outer surface. In an embodiment, the ZIF layer can be characterized by a thickness effective to enable the pressure swing adsorption process, e.g., adsorption step, desorption step, purging step. As will be appreciated by one of skill in the art, and with the help of this disclosure, the thickness of the ZIF layer could depend on the technique used to deposit ZIF particles onto the support, ZIF particle size distribution, etc. In some embodiments, the ZIF layer can be characterized by a thickness of from about 10 nm to about 5 mm, alternatively from about 100 nm to about 1 mm, alternatively from about 500 nm to about 500 microns, alternatively from about 500 nm to about 250 microns, or alternatively from about 1 micron to about 100 microns.

In an embodiment, the support comprises a film, a foil, a mesh, a fiber cloth, a woven fiber mesh, a woven wire mesh, a metallic woven wire mesh, a polymeric membrane, a surface treated material, a surface treated metal foil, a woven fiber cloth, a foam, a polymeric foam, polymeric foam particles, and the like, or combinations thereof.

In some embodiments, the support can be a woven fiber cloth or fiber mesh wherein at least a fraction of fibers are comprised of a ZIF and wherein the remaining fraction is comprised of a non-adsorbent material. In some embodiments, the hydrocarbon adsorber can also be comprised of ZIF crystals or crystallites embedded within the support.

In an embodiment, the dimensions (e.g., thickness) of a support layer can be any effective dimensions. For purposes of the disclosure herein the effective dimensions of a support represents any dimensions (e.g., thickness) capable of providing at least a minimum integrity needed under PSA process conditions for an intended overall structure of a hydrocarbon adsorber bed comprising a hydrocarbon adsorber.

In an embodiment, the support comprises a non-adsorbent material towards hydrocarbons. In such embodiment, the support can be treated by any suitable treating technique to incorporate at least an effective amount of a ZIF on/within the support material. Nonlimiting examples of treating techniques for applying a ZIF to the support suitable for use in the present disclosure include wash coating techniques, in situ crystallization methods that deposit a ZIF directly onto the support from a synthesis solution, doctor-blading, spraying, spray-coating, electrodeposition, dry-wet spinning, or the like.

In an embodiment, the support can be coated with a ZIF by wash-coating. A typical wash-coating process involves a slurry preparation (e.g., ZIF particles, a suitable binder, and optionally a viscosifying agent), slurry application by washing or dipping, drying, and/or sintering. Once a wet coating is formed, such coating has to be dried and sintered at relatively high temperatures (e.g., from about 300° C. to about 600° C.) to establish binding among coating components and adhesion between coating and a surface of the support.

In some embodiments, the hydrocarbon adsorber can further comprise a binder, wherein the binder can facilitate adherence between the ZIF and the support. Nonlimiting examples of binders suitable for use in the present disclosure include a crystalline polymer, a non-crystalline polymer, an epoxy, a thermoplastic polymer, a clay, a silica-containing material, an alumina-containing material, a titania-containing material, and the like, or combinations thereof. In an embodiment, the binder can have a porous structure.

In an embodiment, the support comprises a porous material (e.g., a foamed material) and the ZIF can be applied in a manner in which particles of ZIF fill at least a portion of the pores of a porous structure of the support. For example, a slurry containing ZIF crystals can be soaked into, or pressured through, a porous support material, then such support can be dried and/or calcined (e.g., heated to high temperatures, for example greater than about 300° C.).

As will be appreciated by one of skill in the art and with the help of this disclosure, when the support is in a layer form, a coated support can typically have two major opposing support surfaces, and one or both of these surfaces can be coated with the ZIF.

In an embodiment, the hydrocarbon adsorber can further comprise additives. In such embodiment, additives can be used to improve the adsorption/desorption and transport properties of hydrocarbons within the ZIF. Nonlimiting examples of additives suitable for use in the present disclosure in the hydrocarbon adsorbers include zeolites, microporous crystalline materials, silicates, silicoaluminophosphates (SAPOs), aluminophosphates (AlPOs), high heat capacity materials, high heat conductivity materials, metals, thermally conductive polymers, a porous thermally conductive polymers, foamed thermally conductive polymers, and the like, or combinations thereof. As will be appreciated by one of skill in the art, and with the help of this disclosure, high heat capacity materials and/or high heat conductivity materials can assist in the capture and transfer of at least a portion of the heat that could be generated during adsorption step(s) of the swing adsorption process, thereby decreasing the duration of cycling process, increasing throughput, and further improving the overall efficiency of the ZIF for selective adsorbtion of desired hydrocarbons (e.g., ethane). Further, as will be appreciated by one of skill in the art, and with the help of this disclosure, when the support is a porous thermally conductive polymer and/or a foamed thermally conductive polymer, the ZIF can be present in the pores of such porous and/or foamed support material, whereby the ZIF is structurally supported by the support. Further, as will be appreciated by one of skill in the art, and with the help of this disclosure, the variation in temperature within a hydrocarbon adsorber bed is not expected to be significant, and as such the presence of high heat capacity materials and/or high heat conductivity materials within the hydrocarbon adsorber could mitigate the effects of any heat released during an adsorption step, without the need to cool the hydrocarbon adsorber bed. In some embodiments, the hydrocarbon adsorber bed can be cooled (e.g., external cooling, jacket cooling, internal cooling, coil cooling, etc.).

In an embodiment, the PSA unit 500 can comprise a hydrocarbon adsorber bed, wherein the hydrocarbon adsorber bed comprises a hydrocarbon adsorber. In an embodiment, the hydrocarbon adsorber bed can be assembled by using any suitable methodology compatible with materials and methods disclosed herein. In some embodiments, each PSA unit can comprise more than one hydrocarbon adsorber bed, such as for example, two, three, four, five, six, seven, eight, nine, ten, or more hydrocarbon adsorber beds. In some embodiments, all hydrocarbon adsorber beds within the same PSA unit undergo the same step at the same time, whether the step is an adsorption step, a desorption step, or a purging step. In other embodiments, hydrocarbon adsorber beds within the same PSA unit could be segregated (e.g., separated, partitioned, isolated, etc.) in such a manner that different hydrocarbon adsorber beds within the same PSA unit would undergo different steps during the same time frame. For example, within the same PSA unit, some beds would undergo an adsorption step, while other beds would undergo a desorption step, while some other beds would undergo a purging step, etc. Generally, a PSA unit denotes a collection of processing equipment that is designed to perform the required steps, such as for example an adsorption step, a desorption step, a purging step, etc. Typically, one PSA unit can include one or more hydrocarbon adsorber beds, wherein the hydrocarbon adsorber beds could have different configurations, such as for example the beds could be arranged in series, in parallel, or combinations thereof. Generally, beds can refer to an actual assemblage of material (e.g., hydrocarbon adsorber material). However, the terms "bed" and "unit" should not be construed as limiting and these terms could be used interchangeably for purposes of the disclosure herein. As will be appreciated by one of skill in the art, and with the help of this disclosure, alternative configurations to the PSA unit and bed configurations specifically disclosed herein are possible and such alternative configurations are within the scope of the present disclosure.

In an embodiment, the PSA unit comprises a PSA unit structure wherein one or more hydrocarbon adsorber beds can be housed, and wherein the PSA unit structure can have any suitable geometry. In an embodiment, the PSA unit structure can have a cylindrical geometry.

In an embodiment, the hydrocarbon adsorber bed can be characterized by a bed thickness of from about 0.1 feet(ft) to about 20 ft, alternatively from about 1 ft to about 20 ft, or alternatively from about 2 ft to about 10 ft.

In an embodiment, the PSA unit can comprise a gas mixture inlet and a gas mixture outlet. In some embodiments, open flow channels can be provided through the hydrocarbon adsorber bed or beds for the flow of gaseous mixtures (e.g., light hydrocarbon stream, a sweeping gas stream, etc.), wherein the open flow channels can be continuous between the gas mixture inlet and the gas mixture outlet of the PSA unit. Open flow channels can comprise structurally added elements to the PSA unit, such as for example perforated tubes that enable gas flow, spacers, etc.; spaces between hydrocarbon adsorber particles; hydrocarbon adsorber pores; support pores; etc. In some embodiments, the gas mixture inlet and the gas mixture outlet can be located on a body of the PSA unit structure between two opposite ends of such PSA unit structure. In other embodiments, the gas mixture inlet and the gas mixture outlet can be located on substantially opposite ends of the PSA unit structure. In some other embodiments, the gas mixture inlet and the gas mixture outlet can be located in any suitable location on the PSA unit structure.

In an embodiment, a PSA unit structure can comprise spacers. Generally, spacers can provide a fixed distance between layers or sheets of a structure, such as for example between layers of hydrocarbon adsorbers, between hydrocarbon adsorber beds, etc. The spacers can be either integral to the hydrocarbon adsorber bed, of they can be a non-integral independent material. When spacers are integral to the hydrocarbon adsorber bed (e.g., support), then the spacers could be formed during assembling of the hydrocarbon adsorber bed, such as dimples or corrugations (e.g., within the support) of a predetermined size to provide a desired flow channel volume of the open flow channels. When spacers are not integral to the hydrocarbon adsorber bed, then the spacers can be comprised of any suitable material that can be relatively inactive in the PSA unit and that should not typically decompose under PSA process conditions. Nonlimiting examples of spacer materials suitable for use in the present disclosure include particles, such as glass microspheres, wires of suitable size, and the like, or combinations thereof.

In some embodiments, the PSA unit can comprise a PSA unit structure filled with hydrocarbon adsorber particles, wherein the hydrocarbon adsorber particles are contained within the PSA unit structure, such as for example with the help of screens. As will be appreciated by one of skill in the art, and with the help of this disclosure, a size of a screen opening is smaller than a size of the hydrocarbon adsorber particles.

In other embodiments, the PSA unit can comprise a stacked layered sheet structure. The stacked layered sheet structure can be assembled by first preparing a single layer substructure, then folding it back and forth on itself multiple times until a final desired stacked layered sheet structure can be achieved. Alternatively, the stacked layered sheet structure can be assembled by simply stacking single layer substructures. In an embodiment, a layer of hydrocarbon adsorber can be applied to a sheet of support, as previously described herein.

In yet other embodiments, the PSA unit can comprise a plurality of support layers. In such embodiments, the PSA unit can further comprise spacers, wherein the spacers can define open flow channels. A distance between the support layers can be defined by the dimensions of the spacers.

In still yet other embodiments, the PSA unit can comprise a support in a corrugated form, wherein the support comprises folds or furrows. In such embodiments, either one or both sides of the corrugated support can comprise the hydrocarbon adsorber. Open flow channels can be formed between two opposing corrugated support layers.

PSA units rely on pressure swing adsorption (PSA) as a process for selectively separating at least one gaseous component from a gas mixture (e.g., hydrocarbon mixture, light hydrocarbon stream, etc.). PSA processes rely on the fact that under pressure gases tend to be adsorbed within a pore structure of a porous or microporous adsorbent material (e.g., hydrocarbon adsorber, ZIF, etc.).

Generally, PSA utilizes a solid adsorbent material (e.g., hydrocarbon adsorber, ZIF, etc.) that preferentially retains or adsorbs a more readily adsorbed component (e.g., a first hydrocarbon, ethane, etc.) relative to a less readily adsorbed component (e.g., a second hydrocarbon, ethylene, etc.) of a gas mixture (e.g., hydrocarbon mixture, light hydrocarbon stream, etc.). PSA processes, when operated under certain conditions, allow a selective component or components (e.g., first hydrocarbon, ethane) in a gas mixture to be preferentially adsorbed within the pore structure of porous adsorbent materials (e.g., hydrocarbon adsorber, ZIF) relative to a second component or components (e.g., second hydrocarbon, ethylene) in the gas mixture. An adsorption capacity and/or a selectivity of adsorption for a specific component over another component (i.e., adsorption selectivity) as related to a specific hydrocarbon adsorber can often be improved by operating the PSA process under specific pressure and temperature conditions since both pressure and temperature could influence the adsorption properties of the hydrocarbon adsorbers to a certain extent.

As will be appreciated by one of skill in the art, and with the help of this disclosure, gas adsorption within an adsorption bed (e.g., hydrocarbon adsorber bed) is generally an exothermic process, thereby causing a rise in temperature during such adsorption. Without wishing to be limited by theory, the rise in temperature during an adsorption step of a PSA process is generally minimal due to the high pressure under which the adsorption step occurs. While usually not necessary, in some embodiments, the hydrocarbon adsorber bed can be cooled during an adsorption step. During a desorptionstep, the pressure in the PSA unit can be decreased, thereby causing the desorption of the adsorbed gases. By cyclically swinging the pressure of adsorbent beds, PSA processes can be used to separate gases in a mixture when used with an adsorbent (e.g., hydrocarbon adsorber, ZIF) that is selective for one or more of the components of a gas mixture.

In some embodiments, PSA and temperature swing adsorption (TSA) processes could be used in conjunction with each other. A combined PSA/TSA process can be utilized, for example, by increasing the temperature of the adsorbent materials during the lower pressure purge step of a conventional PSA process to improve the desorption of selectively adsorbed component(s) in the process. A bed temperature can then be reduced (or allowed to be reduced, e.g., allowed to cool) during the adsorption step of a PSA cycle to improve adsorption characteristics of the adsorbent material.

In an embodiment, a hydrocarbon adsorber bed (e.g., hydrocarbon adsorber) can be repeatedly cycled through at least two steps: an adsorption/loading step and a desorption/unloading step (e.g., pressure assisted desorption step). Regeneration or unloading of the hydrocarbon adsorber bed can be achieved by decreasing the pressure within the PSA unit to a pressure effective in desorbing at least a portion of the gas or gases that were adsorbed by the hydrocarbon adsorber during the adsorption step. The desorption step can be assisted with use of a partial pressure purge displacement (e.g., a pressure swing), such as for example running a sweeping gas which can be pressurized (e.g., via one or more compressors) across a hydrocarbon adsorber bed. For purposes of the disclosure herein, any combination of processes that involves a pressure swing desorption step, whether it is used in conjunction with a temperature change process or not, will be referred to as PSA or PSA process.

In an embodiment, the PSA process can be conducted with rapid cycles, in which case it can be referred to as a rapid cycle pressure swing adsorption (RCPSA) process. For purposes of the disclosure herein, the terms PSA and RCPSA can be used interchangeably.

In an embodiment, the pressure swing adsorption unit can be characterized by a cycle time of from about 10 seconds to about 1 hour, alternatively from about 10 seconds to about 50 minutes, alternatively from about 15 seconds to about 40 minutes, alternatively from about 20 seconds to about 30 minutes, alternatively from about 25 seconds to about 20 minutes, or alternatively from about 30 seconds to about 10 minutes. For purposes of the disclosure herein, the cycle time of the PSA unit can be defined as the time between the start of two successive adsorption steps, e.g., a time frame necessary to complete an adsorption step, a desorption step and a purging step that are consecutive.

In an embodiment, a PSA process can be conducted in a PSA unit comprising a hydrocarbon adsorber bed, wherein the hydrocarbon adsorber bed comprises a ZIF, wherein the first hydrocarbon comprises a saturated hydrocarbon (e.g., ethane), wherein the second hydrocarbon comprises an olefin (e.g., ethylene).

In an embodiment, a partial pressure of the first hydrocarbon during the adsorption step is higher than a partial pressure of the first hydrocarbon during the desorption step, thereby allowing for the recovery of at least a portion of the first hydrocarbon during the desorption step and for the regeneration of the hydrocarbon adsorber by depletion of adsorbed components, wherein the regenerated hydrocarbon adsorber can be re-used in a subsequent adsorption step. In an embodiment, lowering the partial pressure of the first hydrocarbon can be accomplished by lowering a total pressure in the PSA unit (e.g., a total pressure that the hydrocarbon adsorber bed is subjected/exposed to; a second pressure) during the desorption step, when compared to a total pressure in the PSA unit during the adsorption step (e.g., a total pressure that the hydrocarbon adsorber bed is subjected/exposed to; a first pressure).

In an embodiment, the PSA process can comprise an adsorption step (e.g., a loading step), a desorption step (e.g., an unloading step), and a purging step. In an embodiment, the adsorption step (e.g., step 2600 of contacting the light hydrocarbon stream with a purged hydrocarbon adsorber) can occur at a first pressure and the desorption step (e.g., step 2700 of contacting the loaded hydrocarbon adsorber with a sweeping gas stream) can occur at a second pressure. In an embodiment, a purging step (e.g., step 2800 of contacting the hydrocarbon adsorber with the sweeping gas stream) can occur at or near the first pressure.

In an embodiment, the first pressure can be in the range of from about 600 kPa to about 3,000 kPa, alternatively from about 1,000 kPa to about 2,700 kPa, or alternatively from about 1,500 kPa to about 2,500 kPa.

In an embodiment, the second pressure can be in the range of from about 10 kPa to about 500 kPa, alternatively from about 50 kPa to about 150 kPa, or alternatively from about 75 kPa to about 125 kPa.

In an embodiment, the first pressure can be greater than the second pressure by equal to or greater than about 400 kPa, alternatively by greater than about 1,000 kPa, or alternatively by greater than about 2,000 kPa.

In an embodiment, the PSA process (e.g., adsorption step, desorption step, purging step) can occur at a temperature of from about −30° C. to about 50° C., alternatively from about −25° C. to about 30° C., or alternatively from about −20° C. to about 25° C. For purposes of the disclosure herein, the temperature of the PSA process is considered not to vary significantly over the course of a cycle, e.g., the temperature of the PSA process does not vary in a manner that interferes with performing the adsorption step, the desorption step, and/or the purging step. In an embodiment, the adsorption step can be characterized by an initial temperature (e.g., a temperature at the beginning of the adsorption step) and a final temperature (e.g., a temperature at the end of the adsorption step). In some embodiments, a difference between an initial temperature and a final temperature, wherein the smaller value is subtracted from the larger value, can be less than about 25° C., alternatively less than about 20° C., alternatively less than about 15° C., alternatively less than about 10° C., alternatively less than about 9° C., alternatively less than about 8° C., alternatively less than about 7° C., alternatively less than about 6° C., alternatively less than about 5° C., alternatively less than about 4° C., alternatively less than about 3° C., alternatively less than about 2° C., or alternatively less than about 1° C.

In an embodiment, the light hydrocarbon stream can be contacted with a hydrocarbon adsorber (e.g., a purged hydrocarbon adsorber) to yield a loaded hydrocarbon adsorber and a non-adsorbed gas stream during an adsorption step (e.g., adsorption step 2600). In such embodiment, the adsorption step can occur at a first pressure. In some embodiments, the light hydrocarbon stream can be characterized by a pressure of from about 600 kPa to about 3,000 kPa, alternatively from about 1,000 kPa to about 2,700 kPa, or alternatively from about 1,500 kPa to about 2,500 kPa. In other embodiments, the light hydrocarbon stream can be pressurized (e.g., via one or more compressors) to a pressure of from about 600 kPa to about 3,000 kPa, alternatively from about 1,000 kPa to about 2,700 kPa, or alternatively from about 1,500 kPa to about 2,500 kPa, prior to step 2600 of contacting the light hydrocarbon stream with a purged hydrocarbon adsorber.

Referring to the embodiments of FIG. 1A and/or FIG. 1B, the light hydrocarbon stream (380 and/or 304) that is emitted from a distillation column (350 and/or 301) can have a pressure that is lower than the first pressure. In such embodiment, the light hydrocarbon stream can be optionally pressurized (e.g., via one or more compressors) to about the first pressure prior to contacting at least a portion of the light hydrocarbon stream with the hydrocarbon adsorber. For example, the light hydrocarbon stream can be sent to one or more compressors for pressurizing prior to contacting with the hydrocarbon adsorber.

In some embodiments, an inert gas (e.g., a gas or gas mixture that does not adsorb onto the hydrocarbon adsorber; a sweeping gas; a spent sweeping gas; etc.) can be introduced to the PSA unit during step 2600 of contacting the light hydrocarbon stream with a purged hydrocarbon adsorber. In such embodiments, the inert gas can comprise isobutane and/or nitrogen. As will be appreciated by one of skill in the art, and with the help of this disclosure, introducing an inert gas (e.g., a sweeping gas) to the PSA unit during step 2600 along with a light hydrocarbon stream can increase the pressure in the PSA unit to a desired value (e.g., first pressure).

In an embodiment, the hydrocarbon adsorber can selectively adsorb ethane versus ethylene. Without wishing to be limited by theory, an adsorption selectivity (S) of a first compound (e.g., a first hydrocarbon, such as for example ethane) versus a second compound (e.g., a second hydrocarbon, such as for example ethylene) for a given pressure and temperature can be calculated based on the following formula $S=(x_1/x_2)(y_2/y_1)$, wherein $x_1$ and $x_2$ are mole fractions in the adsorbed phase of the first compound and of the second compound, respectively, wherein $y_1$ and $y_2$ are mole fractions in the bulk or gas phase of the first compound and of the second compound, respectively, and wherein all mole fractions are given for the pressure and temperature at which the selectivity is being reported.

In an embodiment, the hydrocarbon adsorber can be characterized by an adsorption selectivity of ethane versus ethylene as determined by volumetric adsorption at 298 K and at the first pressure of equal to or greater than about 2, alternatively greater than about 5, alternatively greater than about 7, or alternatively greater than about 10. In an embodiment, the non-adsorbed gas stream 520 can comprise recovered ethylene, e.g., ethylene that was present in the light hydrocarbon stream and was subsequently recovered via the non-adsorbed gas stream.

In an embodiment, the non-adsorbed gas stream 520 can further comprise small amounts of ethane (e.g., ethane that was not adsorbed by the hydrocarbon adsorber). As will be appreciated by one of skill in the art, and with the help of this disclosure, nitrogen and isobutane will not be adsorbed by the hydrocarbon adsorber, and as such the hydrocarbon adsorber is specifically chosen for selectively adsorbing ethane. A small amount of ethylene can be adsorbed by the hydrocarbon adsorber, however, as indicated by the adsorption selectivity of ethane versus ethylene of the hydrocarbon adsorber, the amount of ethylene adsorbed by the hydrocarbon adsorber is much lower than the amount of ethane adsorbed by the hydrocarbon adsorber.

In an embodiment, recovered ethylene comprises at least a portion of the ethylene of the light hydrocarbon stream. In an embodiment, a molar ratio of recovered ethylene to ethylene of the light hydrocarbon stream can be from about 0.1 to about 1, alternatively from about 0.3 to about 0.9, or alternatively from about 0.4 to about 0.8.

In an embodiment, the PEP process 2000 can generally comprise the step 2700 of contacting the loaded hydrocarbon adsorber with a sweeping gas stream to yield a hydrocarbon adsorber and a recovered adsorbed gas stream. Contacting the loaded hydrocarbon adsorber with a sweeping gas stream can yield a hydrocarbon adsorber (e.g., unloaded hydrocarbon adsorber, regenerated hydrocarbon adsorber, etc.) and a recovered adsorbed gas stream 530, wherein the sweeping gas sweeps away the desorbed ethane. In an embodiment, at least a portion of the recovered adsorbed gas stream comprising desorbed ethane can be recycled to an ethylene production process.

As will be appreciated by one of skill in the art, and with the help of this disclosure, a sweeping gas can be used in each of the three steps: adsorption step, desorption step, and/or purging step. During the adsorption step, a feed stream (e.g., light hydrocarbon stream 380, 304) can be communicated to the PSA unit (e.g., PSA unit 500), and a sweeping gas (e.g., sweeping gas stream 510) could also be communicated to the PSA unit to aid with the overall process conditions, such as for example to meet pressure requirements (e.g., first pressure) within the PSA unit. During the adsorption step, at least a portion of the components of the sweeping gas can be recovered in the non-adsorbed gas stream along with other non-adsorbed hydrocarbons (e.g., second hydrocarbon, ethylene, etc.), as the sweeping gas components do not adsorb on the hydrocarbon adsorber. Further, during the desorption step, the pressure in the PSA unit is lower when compared to the desorption step (e.g., second pressure versus first pressure) and a sweeping gas can be communicated to the PSA unit to push through the adsorbed gases (e.g., adsorbed first hydrocarbon, adsorbed ethane, etc.). During the desorption step, at least a portion of the components of the sweeping gas can be recovered in the recovered adsorbed gas stream, along with desorbed hydrocarbons (e.g., desorbed first hydrocarbon, desorbed ethane, etc.). Further, during the purging step, a sweeping gas can be communicated to the PSA unit to purge the PSA unit, wherein the sweeping gas provides for an increased pressure within the PSA unit (e.g., first pressure). During the desorption step, at least a portion of the components of the sweeping gas can be recovered in the spent sweeping gas, wherein a composition of the spent sweeping gas can be about the same as a composition of the sweeping gas.

In an embodiment, a sweeping gas stream 510 can be communicated to the PSA unit 500 during a desorption step to aid in the recovery of the adsorbed hydrocarbons (e.g., adsorbed ethane). Without wishing to be limited by theory, the sweeping gas (e.g., isobutane and/or nitrogen) generally flows through any open spaces of the hydrocarbon adsorber bed (e.g., open flow channels, spaces between hydrocarbon adsorber particles, hydrocarbon adsorber pores, support pores, etc.) and carries away any desorbed hydrocarbons (e.g., desorbed ethane) that it encounters in its path.

In an embodiment, a pressure in the PSA unit can be allowed to decrease during step 2700 of contacting the loaded hydrocarbon adsorber with a sweeping gas stream to the second pressure. In some embodiments, the second pressure can be the atmospheric pressure. In such embodiments, a pressure of the sweeping gas can be the second pressure (e.g., atmospheric pressure). As will be appreciated by one of skill in the art, the atmospheric pressure can be defined as the force per unit area exerted on a surface by the weight of air above that surface in the atmosphere of Earth, and as such the atmospheric pressure can vary depending on where the location is on Earth. Generally, the atmospheric pressure can be considered to have a value of about 100-110 kPa.

In an embodiment, at least a portion of the loaded hydrocarbon adsorber can be contacted with a sweeping gas at a second pressure to yield unloaded hydrocarbon adsorber and desorbed ethane, wherein the desorbed ethane comprises at least a portion of the adsorbed ethane. As will be appreciated by one of skill in the art, and with the help of this disclosure, at least a portion of any other hydrocarbons (e.g., ethylene) that were adsorbed in small amounts along with the ethane by the hydrocarbon adsorber will also be desorbed during desorption step 2700, and will be swept by the sweeping gas along with the desorbed ethane. As will be appreciated by one of skill in the art, and with the help of this disclosure, depending on the value of the second pressure, it is unlikely that the entire amount of adsorbed hydrocarbons (e.g., adsorbed ethane) will be desorbed during the desorption step. Depending on the affinity of the hydrocarbons for the hydrocarbon adsorber, after a first PSA cycle, some amount of hydrocarbons (e.g., residual hydrocarbons, ethane, ethylene, etc.) can remain adsorbed by the hydrocarbon adsorber throughout further adsorption/desorption/purging cycles. As will be appreciated by one of skill in the art, and with the help of this disclosure, the hydrocarbon adsorbers optionally can be calcined (e.g., heated to high temperatures, for example greater than about 300° C.) to remove residual adsorbed hydrocarbons and then returned into the PEP process.

In an embodiment, the recovered adsorbed gas stream 530 comprises sweeping gas and recovered ethane, wherein the recovered ethane comprises at least a portion of the desorbed ethane. As will be appreciated by one of skill in the art, and with the help of this disclosure, any amount of ethylene present in the recovered adsorbed gas stream is very low and its presence is due to a low amount of ethylene being adsorbed by the hydrocarbon adsorber. For purposes of the disclosure herein, the recovered adsorbed gas stream primarily contains a sweeping gas and ethane.

In an embodiment, the desorbed ethane comprises at least a portion of the adsorbed ethane. In an embodiment, the adsorbed ethane comprises at least a portion of the ethane of the light hydrocarbon stream. In an embodiment, the desorbed ethane comprises at least a portion of the ethane of the light hydrocarbon stream. In an embodiment, a molar ratio of desorbed ethane to ethane of the light hydrocarbon stream can be from about 0.1 to about 1, alternatively from about 0.3 to about 0.9, or alternatively from about 0.4 to about 0.8.

In an embodiment, the PEP process 2000 can generally comprise the step 2800 of contacting the hydrocarbon adsorber with the sweeping gas stream to yield the purged hydrocarbon adsorber and a spent sweeping gas. For purposes of disclosure herein, the purging step 2800 could also be referred to as a "priming step" or a "pressurizing step." As will be appreciated by one of skill in the art, and with the help of this disclosure, purging step 2800, along with desorption step 2700, contributes to the regeneration of the hydrocarbon adsorption bed for use in a subsequent adsorption step 2600 of a PSA process. In an embodiment, the spent sweeping gas comprises a sweeping gas and residual hydrocarbons, wherein the residual hydrocarbons comprise at least a portion of any hydrocarbons that were not removed by the sweeping gas during step 2700 of contacting the loaded hydrocarbon adsorber with a sweeping gas stream. In such embodiment, the residual hydrocarbons comprise ethane, ethylene, or combinations thereof. In an embodiment, step 2800 of contacting the hydrocarbon adsorber with the sweeping gas stream occurs at the first pressure.

In an embodiment, the sweeping gas utilized in step 2700 of contacting the loaded hydrocarbon adsorber with a sweeping gas stream has a pressure of about the second pressure. In such embodiment, the sweeping gas can be pressurized (e.g., via one or more compressors) to about the first pressure prior to step 2800 of contacting the hydrocarbon adsorber with the sweeping gas stream. For example, the sweeping gas stream can be sent to one or more compressors for pressurizing prior to contacting with the hydrocarbon adsorber in step 2800.

Without wishing to be limited by theory, the sweeping gas (e.g., isobutane and/or nitrogen) generally flows through any open spaces of the hydrocarbon adsorber bed (e.g., open flow channels, spaces between hydrocarbon adsorber particles, hydrocarbon adsorber pores, support pores, etc.) and carries away any residual hydrocarbons (e.g., ethane, ethylene, etc.) that it encounters in its path. Further, without wishing to be limited by theory, the sweeping gas ensures that the pressure in the entire hydrocarbon adsorber bed is about the first pressure.

In an embodiment, the spent sweeping gas comprises residual hydrocarbons in an amount of less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, alternatively less than about 1 wt. %, based on the total weight of the spent sweeping gas. The spent sweeping gas can be emitted from the PSA unit 500 during the purging step 2800; the recovered adsorbed gas stream 530 can be emitted from the PSA unit 500 during the desorption step 2700; and the non-adsorbed gas stream 520 can be emitted from the PSA unit 500 during the adsorption step 2600. In some embodiments, the recovered adsorbed gas stream 530 and/or the spent sweeping gas can be sent to flare.

In an embodiment, at least a portion of the spent sweeping gas can be recycled to the sweeping gas stream, such as for example to a sweeping gas stream utilized in purging step 2800, to a sweeping gas stream utilized in desorption step 2700, to a sweeping gas stream utilized in adsorption step 2600, etc.

In an embodiment, the spent sweeping gas can be contacted with at least a portion of the light hydrocarbon stream during step 2600 of contacting the light hydrocarbon stream with a purged hydrocarbon adsorber. In such embodiment, the spent sweeping gas can be combined with a sweeping gas stream prior to step 2600 of contacting the light hydrocarbon stream with a purged hydrocarbon adsorber.

In an embodiment, a process (e.g., PSA process) for component separation in a polymer production system (e.g., polyethylene production system) comprising selectively separating a first hydrocarbon (e.g., by-product hydrocarbon, by-product ethane) from a second hydrocarbon (e.g., unreacted monomer, unreacted ethylene) can be a cyclic or loop process (e.g., PSA cyclic process), wherein the cyclic process can comprise three steps: an adsorption step 2600, a desorption step 2700, and a purging step 2800. As will be appreciated by one of skill in the art, and with the help of this disclosure, purging step 2800 of contacting the hydrocarbon adsorber with the sweeping gas stream is the priming step that a hydrocarbon adsorber bed has to undergo, prior to cycling through an adsorption step, a desorption step, and a purging step. Further, as will be appreciated by one of skill in the art, and with the help of this disclosure, purging step 2800 "primes" the hydrocarbon adsorber for entering a PSA cyclic process for component separation. Further, as will be appreciated by one of skill in the art, and with the help of this disclosure, while the first step that a PSA cyclic process comprises can be defined as an adsorption step, such adsorption step necessitates a purged hydrocarbon adsorber, thereby the hydrocarbon adsorber beds have to be purged or primed (e.g., undergo purging step 2800) prior to entering the PSA cycles comprising an adsorption step, a desorption step, and a purging step.

Further, as will be appreciated by one of skill in the art, and with the help of this disclosure, deciding when a step (e.g., adsorption step, desorption step, purging step) ends and it is time to cycle/move a PSA unit onto the subsequent step can be achieved by in-line or real-time monitoring of effluent gas streams. Such in-line monitoring can be achieved by using any suitable analytical tools and methodology, e.g., gas chromatography, mass spectrometry, flame ionization detector, and the like, or combinations thereof. For example, during an adsorption step, the non-adsorbed gas stream can be monitored, and an increase in ethane content of the non-adsorbed gas stream could signal that it is time to cycle the PSA unit to the desorption step. Similarly, for example, during a desorption step, the recovered adsorbed gas stream can be monitored, and a decrease in ethane content of the recovered adsorbed gas stream could signal that it is time to cycle the PSA unit to the purging step.

In an embodiment, a PSA unit comprises at least one hydrocarbon adsorber bed disposed therein. In some embodiments, a PSA unit comprises a plurality of hydrocarbon adsorber beds disposed therein. While the PSA units will be discussed in detail in the context of two and/or three PSA units operating in parallel, it should be understood that any suitable number of PSA units can be used for processing a gas stream (e.g., light hydrocarbon stream, gaseous mixture, hydrocarbon mixture, etc.), such as for example one, two, three, four, five, six, seven, eight, nine, ten, or more PSA units.

In an embodiment, a PSA system can comprise from about 2 to about 8 pressure swing adsorption units operated in parallel, alternatively from about 3 to about 7 pressure swing adsorption units operated in parallel, or alternatively from about 4 to about 6 pressure swing adsorption units operated in parallel.

In an embodiment, the PSA unit 500 as shown in FIG. 1A and/or FIG. 1B comprises at least two PSA units working in parallel.

Figure 4A:
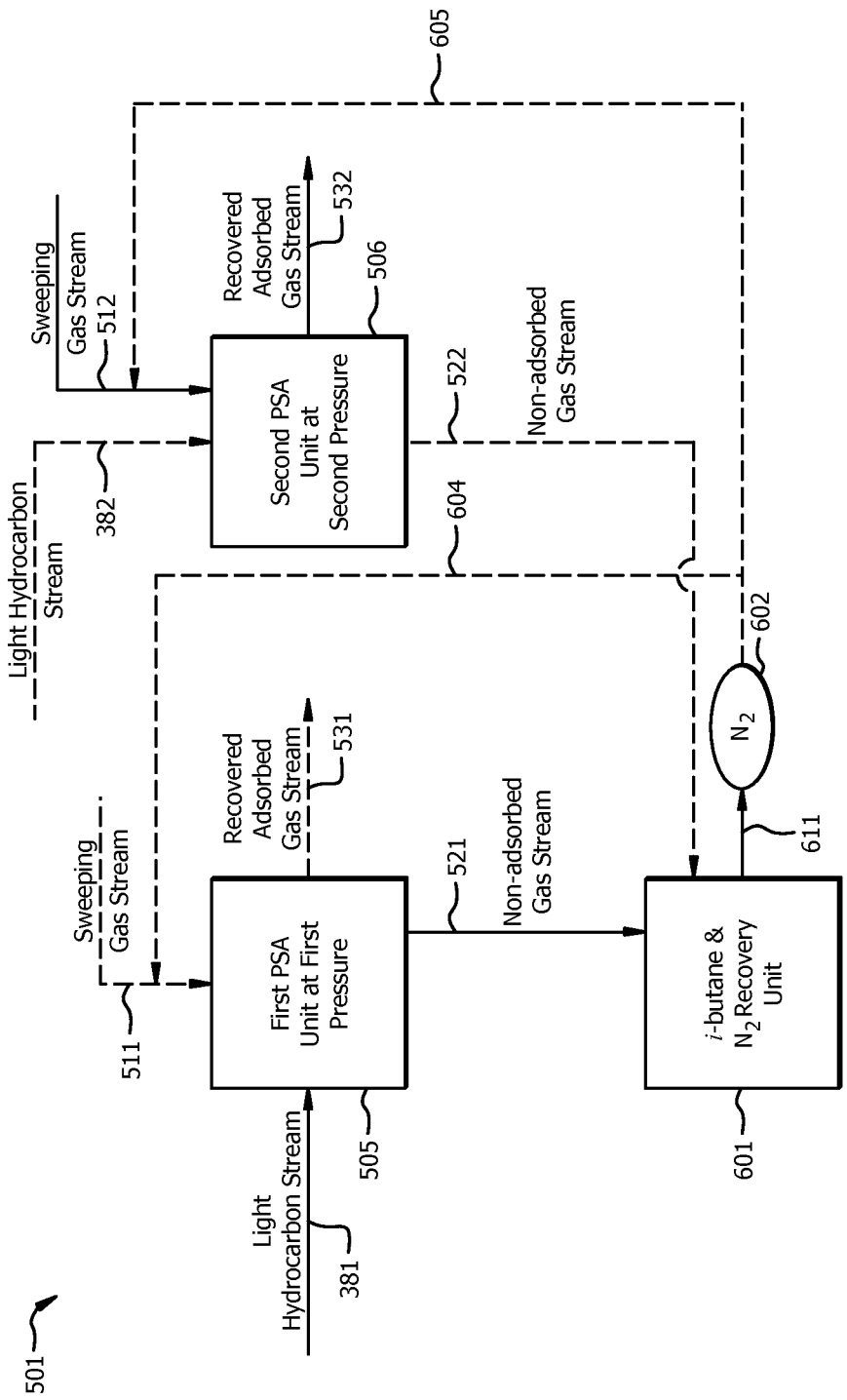
FIG. 4A illustrates a schematic of a first embodiment of a pressure swing adsorption system.

Referring to the embodiment of FIG. 4A, a first PSA system 501 is disclosed. PSA system 501 generally comprises two PSA units operating in parallel. PSA system 501 generally comprises a first PSA unit 505 and a second PSA unit 506. In an embodiment, the first PSA unit 505 and the second PSA unit 506 can operate concurrently or simultaneously. For example, the adsorption step 2600 (e.g., contacting the light hydrocarbon stream with a purged hydrocarbon adsorber to yield a loaded hydrocarbon adsorber and a non-adsorbed gas stream) can occur in the first PSA unit 505 at the first pressure and the desorption step 2700 (e.g., contacting the loaded hydrocarbon adsorber with a sweeping gas stream to yield a hydrocarbon adsorber and a recovered adsorbed gas stream) can occur in the second PSA unit 506 at the second pressure, wherein the first PSA unit and the second PSA unit are operated in parallel. In an embodiment, the purging step 2800 (e.g., contacting the hydrocarbon adsorber with the sweeping gas stream to yield the purged hydrocarbon adsorber and a spent sweeping gas) can occur in the second PSA unit at the first pressure, subsequent to the desorption step 2700. In some embodiments, the purging step 2800 can occur in the second PSA unit while the first PSA unit is still undergoing the adsorption step 2600. In other embodiments, the purging step 2800 can occur in the second PSA unit while the first PSA unit is undergoing a desorption step 2700 subsequent to the adsorption step 2600.

In an embodiment, the first PSA system 501 can comprise a first PSA unit 505 and a second PSA unit 506, wherein the first PSA unit 505 is undergoing desorption step 2700 (subsequent to adsorption step 2600) and wherein the second PSA unit 506 is undergoing adsorption step 2600 (subsequent to desorption step 2700 and purging step 2800). As will be appreciated by one of skill in the art, and with the help of this disclosure, as the PSA units cycle through a PSA process, each PSA unit will successively cycle through each of the cycling steps: an adsorption step, a desorption step, and a purging step, wherein the PSA units are offset such that at any given time one of the units is ready to or undergoing the adsorption step, thereby providing for a continuous process.

Referring to the embodiment of FIG. 4A, a light hydrocarbon stream 381 (e.g., light hydrocarbon stream 380 in FIG. 1A and/or light hydrocarbon stream 304 FIG. 1B) can be communicated to a first PSA unit 505 operating at the first pressure. Optionally, a sweeping gas stream 511 can be communicated to the first PSA unit 505 during the adsorption step 2600. A non-adsorbed gas stream 521 (e.g., non-adsorbed gas stream 520 in FIG. 1A and/or FIG. 1B) can be communicated from the first PSA unit 505 to the INRU 601 (e.g., INRU 600 in FIG. 1A and/or FIG. 1B). A gas stream 611 (e.g., gas stream 610 in FIG. 1A and/or FIG. 1B) comprising nitrogen 602 (e.g., nitrogen 615 in FIG. 1A and/or FIG. 1B) can be emitted from the INRU 601. At least a portion of the nitrogen 602 can be recycled 604 to the first PSA unit 505, for example via the sweeping gas stream 511 (e.g., sweeping gas stream 510 in FIG. 1A and/or FIG. 1B), and/or recycled 605 to the second PSA unit 506, for example via the sweeping gas stream 512 (e.g., sweeping gas stream 510 in FIG. 1A and/or FIG. 1B). A gas stream (e.g., gas stream 620 in FIG. 1A and/or FIG. 1B) comprising isobutane and ethylene (e.g., isobutane and ethylene 625 in FIG. 1A and/or FIG. 1B) can be emitted from the INRU 601.

In an embodiment, when the first PSA unit 505 cycles through a desorption step 2700, a sweeping gas stream 511 can be communicated to the first PSA unit 505, and recovered adsorbed gas stream 531 (e.g., recovered adsorbed gas stream 530 in FIG. 1A and/or FIG. 1B) can be emitted from the first PSA unit 505.

Referring to the embodiment of FIG. 4A, a sweeping gas stream 512 can be communicated to a second PSA unit 506 operating at the second pressure. A recovered adsorbed gas stream 532 (e.g., recovered adsorbed gas stream 530 in FIG. 1A and/or FIG. 1B) can be emitted from the second PSA unit 506 during the desorption step 2700.

In an embodiment, when the second PSA unit 506 cycles through an adsorption step 2600, a light hydrocarbon stream 382 (e.g., light hydrocarbon stream 380 in FIG. 1A and/or light hydrocarbon stream 304 FIG. 1B) can be communicated to the second PSA unit 506, and non-adsorbed gas stream 522 (e.g., non-adsorbed gas stream 520 in FIG. 1A and/or FIG. 1B) can be communicated from the second PSA unit 506 and to the INRU 601.

In an embodiment, the PSA unit 500 as shown in FIG. 1A and/or FIG. 1B comprises at least three PSA units working in parallel.

Figure 4B:
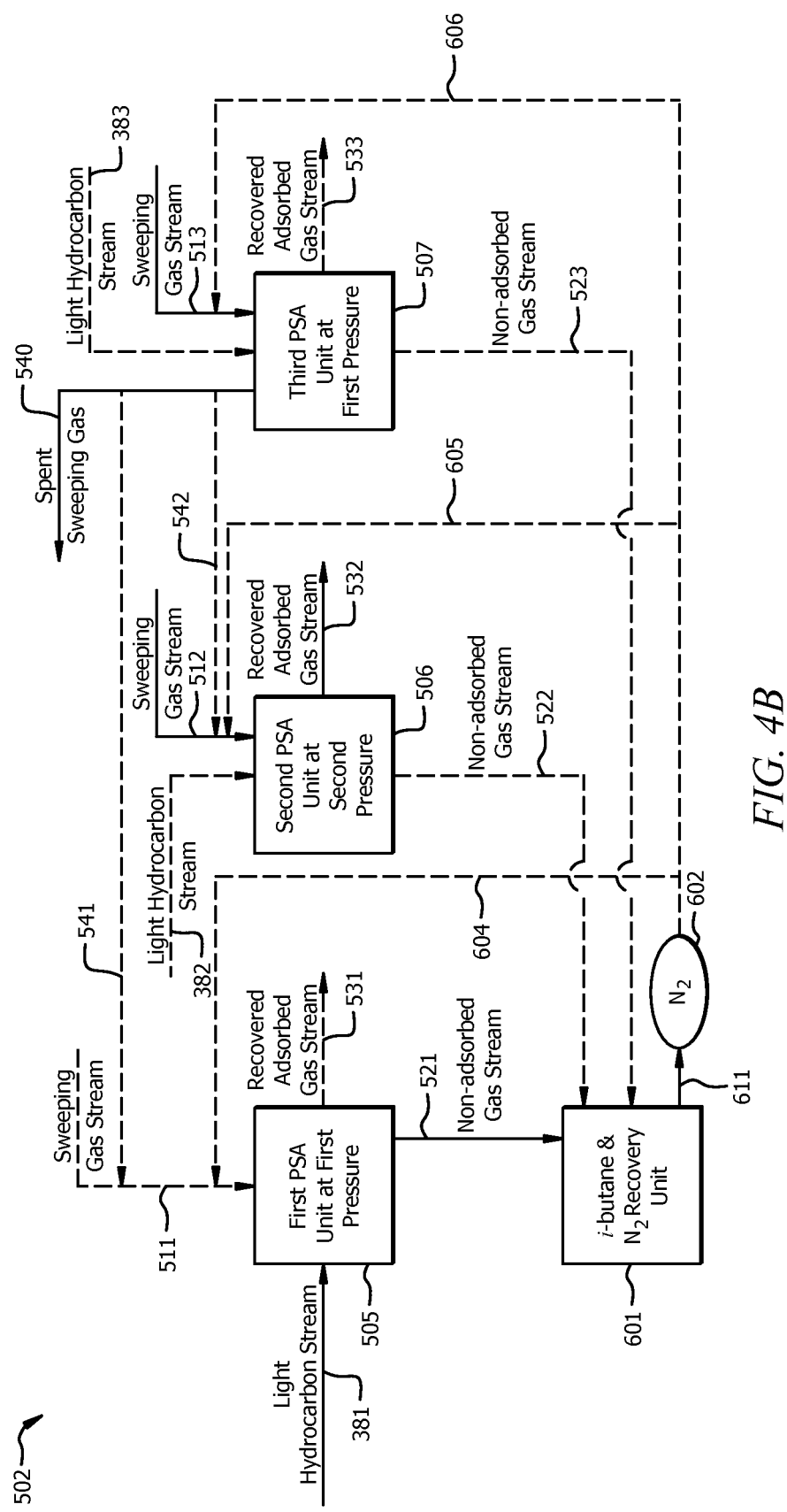
FIG. 4B illustrates a schematic of a second embodiment of a pressure swing adsorption system.

Referring to the embodiment of FIG. 4B, a second PSA system 502 is disclosed, which has a number of system components common with PSA system 501. In the alternative embodiment illustrated by FIG. 4B, the second PSA system 502 comprises three PSA units operating in parallel (as opposed two PSA units operating in parallel of PSA system 501). PSA system 502 generally comprises a first PSA unit 505, a second PSA unit 506, and a third PSA unit 507. In an embodiment, the first PSA unit 505, the second PSA unit 506, and the third PSA unit 507 can operate concurrently or simultaneously. For example, the adsorption step 2600 can occur in the first PSA unit 505 at the first pressure; the desorption step 2700 can occur in the second PSA unit 506 at the second pressure; and the purging step 2800 (e.g., contacting the hydrocarbon adsorber with the sweeping gas stream to yield the purged hydrocarbon adsorber and a spent sweeping gas) can occur in a third PSA unit 507 at the first pressure; wherein the first PSA unit, the second PSA unit, and the third PSA unit are operated in parallel, and wherein the first pressure is greater than the second pressure.

In an embodiment, the second PSA system 502 can comprise a first PSA unit 505, a second PSA unit 506, and a third PSA unit 507, wherein the first PSA unit 505 is undergoing desorption step 2700 (subsequent to adsorption step 2600), wherein the second PSA unit 506 is undergoing purging step 2800 (subsequent to desorption step 2700), and wherein the third PSA unit 507 is undergoing adsorption step 2600 (subsequent to purging step 2800). In an embodiment, the second PSA system 502 can comprise a first PSA unit 505, a second PSA unit 506, and a third PSA unit 507, wherein the first PSA unit 505 is undergoing purging step 2800 (subsequent to desorption step 2700), wherein the second PSA unit 506 is undergoing adsorption step 2600 (subsequent to purging step 2800), and wherein the third PSA unit 507 is undergoing desorption step 2700 (subsequent to adsorption step 2600). As will be appreciated by one of skill in the art, and with the help of this disclosure, as the PSA units cycle through a PSA process, each PSA unit will successively cycle through each of the cycling steps: an adsorption step, a desorption step, and a purging step, wherein the PSA units are offset such that at any given time one of the units is ready to or undergoing the adsorption step, thereby providing for a continuous process.

Referring to the embodiment of FIG. 4B, a sweeping gas stream 513 (e.g., sweeping gas stream 510 in FIG. 1A and/or FIG. 1B) can be communicated to the third PSA unit 507 operating at the first pressure. A spent sweeping gas 540 can be emitted from the third PSA unit 507 during the purging step 2800. At least a portion of the spent sweeping gas 540 can be recycled 541 to the first PSA unit and/or recycled 542 the second PSA unit, such as for example via the sweeping gas stream 511 and/or the sweeping gas stream 512, respectively.

In an embodiment, when the third PSA unit 507 cycles through an adsorption step 2600, a light hydrocarbon stream 383 (e.g., light hydrocarbon stream 380 in FIG. 1A and/or light hydrocarbon stream 304 FIG. 1B) can be communicated to the third PSA unit 507, and non-adsorbed gas stream 523 (e.g., non-adsorbed gas stream 520 in FIG. 1A and/or FIG. 1B) can be communicated from the third PSA unit 507 and to the INRU 601. In such embodiment, at least a portion of the nitrogen 602 can be recycled 606 to the third PSA unit 507, for example via the sweeping gas stream 513 (e.g., sweeping gas stream 510 in FIG. 1A and/or FIG. 1B).

In an embodiment, when the third PSA unit 507 cycles through a desorption step 2700, the sweeping gas stream 513 can be communicated to the third PSA unit 507, and a recovered adsorbed gas stream 533 (e.g., recovered adsorbed gas stream 530 in FIG. 1A and/or FIG. 1B) can be emitted from the third PSA unit 507.

In an embodiment, the PEP process 2000 can generally comprise the step 2900 of separating the non-adsorbed gas stream into a nitrogen stream and an isobutane and ethylene stream. Referring to the embodiments of FIG. 1A and/or FIG. 1B, a non-adsorbed gas stream 520 can be communicated from the PSA unit 500 to the INRU 600. Separating the non-adsorbed gas stream 520 into a nitrogen stream 610 and an isobutane and ethylene stream 620 comprising isobutane and ethylene 625 can be accomplished in the INRU 600.

In an embodiment, INRU 600 can comprise a membrane recovery unit, a pressure swing adsorption unit, a refrigeration unit, and the like. The INRU 600 can separate the non-adsorbed gas stream into the nitrogen stream 610 and the isobutane and ethylene stream 620.

In an embodiment, at least a portion of the nitrogen stream 610 can be recycled 616 to the purge column 400, for example via the purge gas stream 410. In an embodiment, at least a portion of the nitrogen stream 610 can be recycled 617 to the PSA unit 500, for example via the sweeping gas stream 510. Moreover, fresh nitrogen can be added to a nitrogen circuit comprising the purge gas stream 410 and/or a PSA unit 500 to account for nitrogen losses in the purge column 400, in the PSA unit 500 and/or in the INRU 600.

In some embodiments, at least a portion of the isobutane and ethylene 625 comprising ethylene can be pressurized (e.g., via one or more compressors) and re-introduced 626 (e.g., as shown in FIG. 1A and/or FIG. 1B) into a PEP process (e.g., into the slurry loop reactor system 100), for example via the reagents stream 110. In some embodiments, a reintroduction stream 626 can be communicated to the purifier 102. In other embodiments, at least a portion of the isobutane and ethylene 625 comprising ethylene can be optionally cooled in a heat exchanger and collected in a recycle surge tank for feed to a reactor (e.g., reactor 104, reactor 106).

The various embodiments shown in the Figures can be simplified and may not illustrate common equipment such as heat exchangers, pumps, and compressors; however, a skilled artisan would recognize the disclosed processes and systems may include such equipment commonly used throughout polymer manufacturing.

A skilled artisan will recognize that industrial and commercial polyethylene manufacturing processes can necessitate one or more, often several, compressors or similar apparatuses. Such compressors are used throughout polyethylene manufacturing, for example to pressurize reactors 104, 106 during polymerization. Further, a skilled artisan will recognize that a polyethylene manufacturing process includes one or more deoxygenators and/or similar de-oxidizing apparatuses, for instance for purifying solvents or reactants and/or for purging reactors of oxygen. Because the infrastructure and the support therefore, for example to provide power and maintain the compressors and/or deoxygenators, already exists within a commercial polyethylene manufacturing plant, reallocating a portion of these available resources for use in the disclosed systems can necessitate little, if any, additional capital expenditure in order to incorporate the disclosed systems and or processes.

Further, because compressors, deoxygenators, and various other components are already employed in various polyethylene processes and systems, the opportunity for increased operation of such apparatuses can improve the overall efficiency of polyethylene production systems and processes. For example, when a portion of a PEP process or system is taken off-line for maintenance and/or repair, other portions of the system (e.g., a compressor, a deoxygenator, a reactor, etc.) can continue to provide service according to the current processes. Operating and/or reallocating resources for operation of the disclosed PEP systems and/or processes can thereby increase the efficiency with which conventional systems are used.

In an embodiment, a process for component (e.g., hydrocarbon) separation in a polymer production system (e.g., polyethylene production system) can comprise the steps of (a) separating a polymerization product stream into a gas stream and a polymer stream; (b) processing the gas stream in one or more distillation columns to yield a light hydrocarbon stream, wherein the light hydrocarbon stream comprises ethylene and ethane; (c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a pressure of about 2,200 kPa to yield adsorbed ethane, wherein the non-adsorbed gas stream comprises recovered ethylene, wherein the recovered ethylene comprises at least a portion of the ethylene of the light hydrocarbon stream, wherein the light hydrocarbon stream is characterized by a temperature of about −25° C., wherein the hydrocarbon adsorber is characterized by an adsorption selectivity of ethane versus ethylene as determined by volumetric adsorption at 298 K and at a pressure of about 2,200 kPa of equal to or greater than about 2, and wherein the hydrocarbon adsorber comprises a zeolitic imidazolate framework (ZIF) selected from ZIF-7, ZIF-8, or both ZIF-7 and ZIF-8; (d) contacting at least a portion of the loaded hydrocarbon adsorber with a sweeping gas stream at a pressure of about 110 kPa to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the sweeping gas stream comprises isobutane and/or nitrogen; and (e) contacting at least a portion of the unloaded hydrocarbon adsorber with at least a portion of the sweeping gas stream at a pressure of about 2,200 kPa to yield the purged hydrocarbon adsorber and a spent sweeping gas.

In an embodiment, a process for hydrocarbon recovery can comprise the steps of (a) providing a hydrocarbon stream comprising a first hydrocarbon and a second hydrocarbon, wherein the first hydrocarbon is a saturated hydrocarbon, and wherein the second hydrocarbon is an olefin; (b) contacting at least a portion of the hydrocarbon stream with a purged hydrocarbon adsorber to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, and wherein the non-adsorbed gas stream comprises recovered second hydrocarbon, wherein the recovered second hydrocarbon comprises at least a portion of the second hydrocarbon of the hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2; (c) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed first hydrocarbon, wherein the desorbed first hydrocarbon comprises at least a portion of the adsorbed first hydrocarbon, and wherein the first pressure is greater than the second pressure by equal to or greater than about 400 kPa; and (d) contacting at least a portion of the unloaded hydrocarbon adsorber with at least a portion of the sweeping gas stream at the first pressure to yield the purged hydrocarbon adsorber and a spent sweeping gas. In such embodiment, the first hydrocarbon can comprise ethane, the second hydrocarbon can comprise ethylene, and the sweeping gas can comprise isobutane and/or nitrogen.

In an embodiment, a pressure swing adsorption system can comprise at least two pressure swing adsorption units, wherein the adsorption step, the desorption step, and the purging step are offset (do not occur simultaneously within the same PSA unit) between the at least two pressure swing adsorption units; wherein the at least two pressure swing adsorption units are operated in parallel; wherein the pressure swing adsorption unit comprises at least one hydrocarbon adsorber bed disposed therein; wherein the hydrocarbon adsorber bed comprises a hydrocarbon adsorber; wherein the hydrocarbon adsorber is contacted with a sweeping gas stream to yield a purged hydrocarbon adsorber; wherein the pressure swing adsorption unit adsorbs at a first pressure, wherein the purged hydrocarbon adsorber adsorbs a first hydrocarbon to yield a loaded hydrocarbon adsorber comprising an adsorbed first hydrocarbon and a non-adsorbed gas stream comprising a second hydrocarbon; wherein the hydrocarbon adsorber has an adsorption selectivity of the first hydrocarbon versus the second hydrocarbon as determined by volumetric adsorption at 298 K and at the first pressure of equal to or greater than about 2; wherein the pressure swing adsorption unit regenerates at a second pressure, wherein the loaded hydrocarbon adsorber is regenerated to yield an unloaded hydrocarbon adsorber, and a desorbed first hydrocarbon; wherein the first pressure is greater than the second pressure by equal to or greater than about 400 kPa; and wherein the unloaded hydrocarbon adsorber is contacted with a sweeping gas stream to yield a purged hydrocarbon adsorber. In such embodiment, the first hydrocarbon can comprise ethane, the second hydrocarbon can comprise ethylene, and the hydrocarbon adsorber bed can have a bed thickness of from about 1 ft to about 20 ft.

In an embodiment, one or more of the disclosed systems (e.g., PEP system 1000, PEP system 1001) and/or processes (e.g., PEP process 2000) can advantageously display improvements in one or more system and/or process characteristics when compared to otherwise similar systems and/or processes lacking a step of ethylene recovery in a PSA unit. In an embodiment, the PSA unit as disclosed herein can advantageously allow for the recovery of a substantial portion of ethylene that would otherwise be lost due to conventional operation of such systems or processes, for example, by flaring. In an embodiment, one or more of the disclosed systems can allow for the recovery of up to about 75%, alternatively, up to about 85%, alternatively, up to about 90%, alternatively, up to about 95% by total weight of ethylene from a light hydrocarbon stream that would otherwise be lost. The recovery of such a portion of ethylene (e.g., unreacted ethylene monomers) can yield a significant economic benefit, for example, by improving the efficiency of usage of ethylene and decreasing capital inputs associated with the acquisition of ethylene.

In an embodiment, the PSA unit as disclosed herein can advantageously decrease the amount of ethane that is returned to a polymerization reactor (such as reactors 104 and/or 106) via a recycle stream (e.g., stream 626). By decreasing the amount of ethane contained in a stream to a polymerization reactor, the overall efficiency of the polyethylene production can be improved (for example, by increasing the ethylene concentration without reaching a bubble point in the loop reactor). For example, decreasing the amount of ethane in a stream can improve polymerization reactor efficiency, improve catalyst efficiency, reduce polymer fouling, reduce polymerization downtime, improve production of bimodal polymer types, improve production of copolymers, or combinations thereof.

In an embodiment, the PSA unit as disclosed herein can advantageously reduce a load on a compressor of the INRU due to a reduced gas stream throughput through such compressor. In some embodiments where the INRU comprises a pressure swing adsorption bed, such bed can advantageously display an increased capacity for isobutane adsorption, owing to the decreased content of ethane in the gas stream entering the INRU. In other embodiments where the INRU comprises a membrane recovery unit, such membrane can advantageously display an increased throughput of isobutane, owing to the decreased content of ethane in the gas stream entering the INRU. Additional advantages of the systems and/or processes for the production of a polyethylene polymer as disclosed herein can be apparent to one of skill in the art viewing this disclosure.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

Additional Disclosure

A first embodiment, which is a process for component separation in a polymer production system, the process comprising:

(a) separating a polymerization product stream into a gas stream and a polymer stream;

(b) processing the gas stream in one or more distillation columns to yield a light hydrocarbon stream, wherein the light hydrocarbon stream comprises ethylene and ethane;

(c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream;

(d) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, and wherein the desorbed ethane comprises at least a portion of the adsorbed ethane; and (e) contacting at least a portion of the unloaded hydrocarbon adsorber with at least a portion of the sweeping gas stream at the first pressure to yield the purged hydrocarbon adsorber and a spent sweeping gas.

A second embodiment, which is the process of the first embodiment, wherein the hydrocarbon adsorber is characterized by an adsorption selectivity of ethane versus ethylene as determined by volumetric adsorption at 298 K and at the first pressure of equal to or greater than about 2.

A third embodiment, which is the process of any of the first through the second embodiments, wherein the first pressure is greater than the second pressure by equal to or greater than about 400 kPa.

A fourth embodiment, which is the process of any of the first through the third embodiments, wherein the first pressure is from about 600 kPa to about 3,000 kPa.

A fifth embodiment, which is the process of any of the first through the fourth embodiments, wherein (c) contacting the light hydrocarbon stream with the purged hydrocarbon adsorber, (d) contacting the loaded hydrocarbon adsorber with the sweeping gas stream, and (e) contacting the unloaded hydrocarbon adsorber with the sweeping gas stream occur at a temperature of from about −30° C. to about 50° C.

A sixth embodiment, which is the process of any of the first through the fifth embodiments, wherein the light hydrocarbon stream obtained by (b) processing the gas stream has a pressure of from about 600 kPa to about 3,000 kPa.

A seventh embodiment, which is the process of any of the first through the sixth embodiments, wherein the light hydrocarbon stream obtained by (b) processing the gas stream is further pressurized to a pressure of from about 600 kPa to about 3,000 kPa prior to (c) contacting with the purged hydrocarbon adsorber.

An eighth embodiment, which is the process of any of the first through the seventh embodiments, wherein a molar ratio of desorbed ethane to ethane of the light hydrocarbon stream is from about 0.1 to about 1.

A ninth embodiment, which is the process of any of the first through the eighth embodiments, wherein a molar ratio of recovered ethylene to ethylene of the light hydrocarbon stream is from about 0.1 to about 1.

A tenth embodiment, which is the process of any of the first through the ninth embodiments, wherein at least a portion of the sweeping gas stream and/or at least a portion of the spent sweeping gas is contacted with at least a portion of the light hydrocarbon stream during (c) contacting with the purged hydrocarbon adsorber.

An eleventh embodiment, which is the process of any of the first through the tenth embodiments, wherein the sweeping gas stream comprises isobutane and/or nitrogen.

A twelfth embodiment, which is the process of any of the first through the eleventh embodiments, wherein at least a portion of the non-adsorbed gas stream is separated into a nitrogen stream and an isobutane and ethylene stream.

A thirteenth embodiment, which is the process of the twelfth embodiment, wherein at least a portion of the isobutane and ethylene stream is recycled as a reagent for the polymer production system.

A fourteenth embodiment, which is the process of any of the twelfth through the thirteenth embodiments, wherein at least a portion of the nitrogen stream is recycled to the sweeping gas stream.

A fifteenth embodiment, which is the process of any of the twelfth through the fourteenth embodiments, wherein at least a portion of the nitrogen stream is recycled to a purge gas stream contacting at least a portion of the polymer stream.

A sixteenth embodiment, which is the process of any of the first through the fifteenth embodiments, wherein at least a portion of the gas stream is distilled into a light distillation bottoms stream comprising olefin-free isobutane, wherein at least a portion of the light distillation bottoms stream is recycled to the sweeping gas stream.

A seventeenth embodiment, which is the process of any of the first through the sixteenth embodiments, wherein at least a portion of the spent sweeping gas is recycled to the sweeping gas stream.

An eighteenth embodiment, which is the process of any of the first through the seventeenth embodiments, wherein at least a portion of the recovered adsorbed gas stream is recycled to an ethylene production process.

A nineteenth embodiment, which is the process of any of the first through the eighteenth embodiments, wherein the hydrocarbon adsorber is part of a pressure swing adsorption unit.

A twentieth embodiment, which is the process of any of the first through the nineteenth embodiments, wherein (c) contacting the light hydrocarbon stream with the purged hydrocarbon adsorber occurs in a pressure swing adsorption unit.

A twenty-first embodiment, which is the process of the nineteenth embodiment, wherein the pressure swing adsorption unit is characterized by a cycle time of from about 10 seconds to about 1 hour.

A twenty-second embodiment, which is the process of any of the nineteenth through the twenty-first embodiments, wherein from about 2 to about 8 pressure swing adsorption units are operated in parallel.

A twenty-third embodiment, which is the process of any of the first through the twenty-second embodiments, wherein (c) contacting the light hydrocarbon stream with the purged hydrocarbon adsorber occurs in a first pressure swing adsorption unit and (d) contacting the loaded hydrocarbon adsorber with the sweeping gas stream and (e) contacting the unloaded hydrocarbon adsorber with the sweeping gas stream occur in a second pressure swing adsorption unit, wherein the first pressure swing adsorption unit and the second pressure swing adsorption unit are operated in parallel.

A twenty-fourth embodiment, which is the process of any of the first through the twenty-third embodiments, wherein (c) contacting the light hydrocarbon stream with the purged hydrocarbon adsorber occurs in a first pressure swing adsorption unit; (d) contacting the loaded hydrocarbon adsorber with the sweeping gas stream occurs in a second pressure swing adsorption unit; and (e) contacting the unloaded hydrocarbon adsorber with the sweeping gas stream occur in a third pressure swing adsorption unit, wherein the first pressure swing adsorption unit, the second pressure swing adsorption unit and the third pressure swing adsorption unit are operated in parallel.

A twenty-fifth embodiment, which is the process of any of the first through the twenty-fourth embodiments, wherein the hydrocarbon adsorber comprises a zeolitic imidazolate framework (ZIF).

A twenty-sixth embodiment, which is the process of the twenty-fifth embodiment, wherein the zeolitic imidazolate framework is characterized by a pore window size of from about 0.2 nm to about 0.5 nm.

A twenty-seventh embodiment, which is the process of any of the twenty-fifth through the twenty-sixth embodiments, wherein the zeolitic imidazolate framework comprises ZIF-7, ZIF-8, ZIF-65, ZIF-67, or combinations thereof.

A twenty-eighth embodiment, which is the process of any of the first through the twenty-seventh embodiments, wherein the hydrocarbon adsorber is in the form of particles, pellets, beads, hollow beads, spheres, ovals, fibers, hollow fibers, tubes, hollow tubes, rods, platelets, disks, plates, ribbons, or combinations thereof.

A twenty-ninth embodiment, which is the process of any of the first through the twenty-eighth embodiments, wherein the hydrocarbon adsorber is characterized by a particle size of from about 0.1 mm to about 5 mm.

A thirtieth embodiment, which is the process of any of the first through the twenty-ninth embodiments, wherein the hydrocarbon adsorber further comprises a support.

A thirty-first embodiment, which is the process of the thirtieth embodiment, wherein the zeolitic imidazolate framework contacts at least a portion of the support, is distributed throughout the support, or combinations thereof.

A thirty-second embodiment, which is the process of any of the thirtieth through the thirty-first embodiments, wherein the support has a porosity of from about 0 vol. % to about 99 vol. % based on the total volume of the support.

A thirty-third embodiment, which is the process of any of the thirtieth through the thirty-second embodiments, wherein the support comprises a support outer surface, wherein at least a portion of the support outer surface is in contact with the zeolitic imidazolate framework.

A thirty-fourth embodiment, which is a process for component separation in a polymer production system, the process comprising:
  (a) separating a polymerization product stream into a gas stream and a polymer stream;

(b) processing the gas stream in one or more distillation columns to yield a light hydrocarbon stream, wherein the light hydrocarbon stream comprises ethylene and ethane;

(c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a pressure of from about 1,000 kPa to about 2,700 kPa to yield adsorbed ethane, wherein the non-adsorbed gas stream comprises recovered ethylene, wherein the recovered ethylene comprises at least a portion of the ethylene of the light hydrocarbon stream, wherein the light hydrocarbon stream is characterized by a temperature of from about −25° C. to about 30° C., wherein the hydrocarbon adsorber is characterized by an adsorption selectivity of ethane versus ethylene as determined by volumetric adsorption at 298 K and at a pressure of from about 1,000 kPa to about 2,700 kPa of equal to or greater than about 2, and wherein the hydrocarbon adsorber comprises a zeolitic imidazolate framework (ZIF) selected from ZIF-7, ZIF-8, or both ZIF-7 and ZIF-8;

(d) contacting at least a portion of the loaded hydrocarbon adsorber with a sweeping gas stream at a pressure of from about 50 kPa to about 150 kPa to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the sweeping gas stream comprises isobutane and/or nitrogen; and (e) contacting at least a portion of the unloaded hydrocarbon adsorber with at least a portion of the sweeping gas stream at a pressure of from about 1,000 kPa to about 2,700 kPa to yield the purged hydrocarbon adsorber and a spent sweeping gas.

A thirty-fifth embodiment, which is a process for component separation in a polymer production system, the process comprising:

(a) separating a polymerization product stream into a gas stream and a polymer stream;

(b) processing the gas stream in one or more distillation columns to yield a light hydrocarbon stream, wherein the light hydrocarbon stream comprises a first hydrocarbon and a second hydrocarbon;

(c) contacting at least a portion of the light hydrocarbon stream with a purged hydrocarbon adsorber to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, and wherein the non-adsorbed gas stream comprises recovered second hydrocarbon, wherein the recovered second hydrocarbon comprises at least a portion of the second hydrocarbon of the light hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2;

(d) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed first hydrocarbon, wherein the desorbed first hydrocarbon comprises at least a portion of the adsorbed first hydrocarbon, and wherein the first pressure is greater than the second pressure by equal to or greater than about 400 kPa; and (e) contacting at least a portion of the unloaded hydrocarbon adsorber with at least a portion of the sweeping gas stream at the first pressure to yield the purged hydrocarbon adsorber and a spent sweeping gas.

A thirty-sixth embodiment, which is a process for hydrocarbon recovery, the process comprising:

(a) providing a hydrocarbon stream comprising a first hydrocarbon and a second hydrocarbon, wherein the first hydrocarbon is a saturated hydrocarbon, and wherein the second hydrocarbon is an olefin;

(b) contacting at least a portion of the hydrocarbon stream with a purged hydrocarbon adsorber to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, and wherein the non-adsorbed gas stream comprises recovered second hydrocarbon, wherein the recovered second hydrocarbon comprises at least a portion of the second hydrocarbon of the hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2;

(c) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed first hydrocarbon, wherein the desorbed first hydrocarbon comprises at least a portion of the adsorbed first hydrocarbon, and wherein the first pressure is greater than the second pressure by equal to or greater than about 400 kPa; and (d) contacting at least a portion of the unloaded hydrocarbon adsorber with at least a portion of the sweeping gas stream at the first pressure to yield the purged hydrocarbon adsorber and a spent sweeping gas.

A thirty-seventh embodiment, which is a pressure swing adsorption system comprising at least two pressure swing adsorption units;

wherein the at least two pressure swing adsorption units are operated in parallel;

wherein the pressure swing adsorption unit comprises at least one hydrocarbon adsorber bed disposed therein;

wherein the hydrocarbon adsorber bed comprises a hydrocarbon adsorber;

wherein the hydrocarbon adsorber is contacted with a sweeping gas stream to yield a purged hydrocarbon adsorber;

wherein the pressure swing adsorption unit adsorbs at a first pressure, wherein the purged hydrocarbon adsorber adsorbs a first hydrocarbon to yield a loaded hydrocarbon adsorber comprising an adsorbed first hydrocarbon and a non-adsorbed gas stream comprising a second hydrocarbon;

wherein the hydrocarbon adsorber has an adsorption selectivity of the first hydrocarbon versus the second hydrocarbon as determined by volumetric adsorption at 298 K and at the first pressure of equal to or greater than about 2;

wherein the pressure swing adsorption unit regenerates at a second pressure, wherein the loaded hydrocarbon adsorber is regenerated to yield an unloaded hydrocarbon adsorber, and a desorbed first hydrocarbon;

wherein the first pressure is greater than the second pressure by equal to or greater than about 400 kPa; and wherein the unloaded hydrocarbon adsorber is contacted with a sweeping gas stream to yield a purged hydrocarbon adsorber.

A thirty-eighth embodiment, which is the pressure swing adsorption system of the thirty-seventh embodiment, wherein the hydrocarbon adsorber bed has a bed thickness of from about 0.1 ft to about 20 ft.

A thirty-ninth embodiment, which is a process for ethylene polymerization, the process comprising:

(a) polymerizing ethylene in a slurry loop reactor system to obtain a polymerization product stream;

(b) separating a polymerization product stream in a flash chamber into a gas stream and a polymer stream;

(c) processing the gas stream in one or more distillation columns to yield a light hydrocarbon stream, wherein the light hydrocarbon stream comprises ethane and ethylene;

(d) contacting at least a portion of the light hydrocarbon stream with a purged hydrocarbon adsorber to yield a loaded hydrocarbon adsorber and a non-adsorbed gas stream, wherein at least a portion of ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream, wherein the hydrocarbon adsorber is characterized by an adsorption selectivity of ethane versus ethylene as determined by volumetric adsorption at 298 K and at the first pressure of equal to or greater than about 2;

(e) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the first pressure is greater than the second pressure by equal to or greater than about 400 kPa; and (f) contacting at least a portion of the unloaded hydrocarbon adsorber with at least a portion of the sweeping gas stream at the first pressure to yield the purged hydrocarbon adsorber and a spent sweeping gas.

A fortieth embodiment, which is the process of the thirty-ninth embodiment, wherein at least a portion of the sweeping gas stream and/or at least a portion of the spent sweeping gas is contacted with at least a portion of the light hydrocarbon stream during (d) contacting with the purged hydrocarbon adsorber;

wherein at least a portion of the non-adsorbed gas stream is separated into a nitrogen stream and an isobutane and ethylene stream;

wherein at least a portion of the isobutane and ethylene stream is recycled as a reagent for (a) polymerizing ethylene;

wherein at least a portion of the nitrogen stream is recycled to the sweeping gas stream; wherein at least a portion of the nitrogen stream is recycled to a purge gas stream contacting at least a portion of the polymer stream;

wherein at least a portion of the gas stream is distilled into a light distillation bottoms stream comprising olefin-free isobutane, wherein at least a portion of the light distillation bottoms stream is recycled to the sweeping gas stream;

wherein at least a portion of the spent sweeping gas is recycled to the sweeping gas stream; and wherein at least a portion of the recovered adsorbed gas stream is recycled to an ethylene production process.

A forty-first embodiment, which is a process for hydrocarbon recovery, the process comprising:

(a) providing a hydrocarbon stream originating from a polymerization process, wherein the hydrocarbon stream comprises a first hydrocarbon and a second hydrocarbon, wherein the first hydrocarbon is a saturated hydrocarbon, and wherein the second hydrocarbon is an olefin;

(b) loading a purged hydrocarbon adsorber with at least a portion of the first hydrocarbon to yield a loaded hydrocarbon adsorber and a non-adsorbed gas stream, wherein at least a portion of the first hydrocarbon is adsorbed by the purged hydrocarbon adsorber at a first pressure to yield adsorbed first hydrocarbon, wherein the loaded hydrocarbon adsorber comprises the adsorbed first hydrocarbon, wherein the non-adsorbed gas stream comprises recovered second hydrocarbon, wherein the recovered second hydrocarbon comprises at least a portion of the second hydrocarbon of the hydrocarbon stream, wherein the hydrocarbon adsorber is characterized by an adsorption selectivity of the first hydrocarbon versus the second hydrocarbon as determined by volumetric adsorption at 298 K and at the first pressure of equal to or greater than about 2;

(c) unloading the loaded hydrocarbon adsorber to yield an unloaded hydrocarbon adsorber and a recovered adsorbed gas stream, wherein a sweeping gas contacts at least a portion of the loaded hydrocarbon adsorber, wherein the adsorbed first hydrocarbon desorbs to yield a desorbed first hydrocarbon and the unloaded hydrocarbon adsorber, wherein the desorbed first hydrocarbon comprises at least a portion of the adsorbed first hydrocarbon, wherein the recovered adsorbed gas stream comprises at least a portion of the sweeping gas stream and at least a portion of the desorbed first hydrocarbon, and wherein the first pressure is greater than the second pressure by equal to or greater than about 400 kPa; and (d) purging the unloaded hydrocarbon adsorber with at least a portion of the sweeping gas stream at the first pressure to yield the purged hydrocarbon adsorber and a spent sweeping gas.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_e-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

We claim:

1. A process for component separation in a polymer production system, the process comprising:
    (a) separating a polymerization product stream into a gas stream and a polymer stream;
    (b) processing the gas stream in one or more distillation columns to yield a light hydrocarbon stream, wherein the light hydrocarbon stream comprises ethylene and ethane;
    (c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream;
    (d) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, and wherein the desorbed ethane comprises at least a portion of the adsorbed ethane; and
    (e) contacting at least a portion of the unloaded hydrocarbon adsorber with at least a portion of the sweeping gas stream at the first pressure to yield the purged hydrocarbon adsorber and a spent sweeping gas.

2. The process of claim 1, wherein the hydrocarbon adsorber is characterized by an adsorption selectivity of ethane versus ethylene as determined by volumetric adsorption at 298 K and at the first pressure of equal to or greater than about 2.

3. The process of claim 1, wherein the first pressure is greater than the second pressure by equal to or greater than about 400 kPa.

4. The process of claim 1, wherein the first pressure is from about 600 kPa to about 3,000 kPa.

5. The process of claim 1, wherein (c) contacting the light hydrocarbon stream with the purged hydrocarbon adsorber, (d) contacting the loaded hydrocarbon adsorber with the sweeping gas stream, and (e) contacting the unloaded hydrocarbon adsorber with the sweeping gas stream occur at a temperature of from about −30° C. to about 50° C.

6. The process of claim 1, wherein the light hydrocarbon stream obtained by (b) processing the gas stream has a pressure of from about 600 kPa to about 3,000 kPa.

7. The process of claim 1, wherein a molar ratio of desorbed ethane to ethane of the light hydrocarbon stream is from about 0.1 to about 1.

8. The process of claim 1, wherein a molar ratio of recovered ethylene to ethylene of the light hydrocarbon stream is from about 0.1 to about 1.

9. The process of claim 1, wherein the sweeping gas stream comprises isobutane and/or nitrogen.

10. The process of claim 1, wherein the hydrocarbon adsorber is part of a pressure swing adsorption unit.

11. The process of claim 1, wherein (c) contacting the light hydrocarbon stream with the purged hydrocarbon adsorber occurs in a pressure swing adsorption unit.

12. The process of claim 10, wherein the pressure swing adsorption unit is characterized by a cycle time of from about 10 seconds to about 1 hour.

13. The process of claim 10, wherein from about 2 to about 8 pressure swing adsorption units are operated in parallel.

14. The process of claim 1, wherein (c) contacting the light hydrocarbon stream with the purged hydrocarbon adsorber occurs in a first pressure swing adsorption unit; (d) contacting the loaded hydrocarbon adsorber with the sweeping gas stream occurs in a second pressure swing adsorption unit; and (e) contacting the unloaded hydrocarbon adsorber with the sweeping gas stream occur in a third pressure swing adsorption unit, wherein the first pressure swing adsorption unit, the second pressure swing adsorption unit and the third pressure swing adsorption unit are operated in parallel.

15. The process of claim 1, wherein the hydrocarbon adsorber comprises a zeolitic imidazolate framework (ZIF).

16. The process of claim 15, wherein the zeolitic imidazolate framework is characterized by a pore window size of from about 0.2 nm to about 0.5 nm.

17. The process of claim 15, wherein the zeolitic imidazolate framework comprises ZIF-7, ZIF-8, ZIF-65, ZIF-67, or combinations thereof.

18. The process of claim 1, wherein the hydrocarbon adsorber is in the form of particles, pellets, beads, hollow beads, spheres, ovals, fibers, hollow fibers, tubes, hollow tubes, rods, platelets, disks, plates, ribbons, or combinations thereof.

19. The process of claim 1, wherein the hydrocarbon adsorber is characterized by a particle size of from about 0.1 mm to about 5 mm.

20. The process of claim 15, wherein the hydrocarbon adsorber further comprises a support, and wherein the zeolitic imidazolate framework contacts at least a portion of the support, is distributed throughout the support, or combinations thereof.

21. A process for component separation in a polymer production system, the process comprising:
    (a) separating a polymerization product stream into a gas stream and a polymer stream;
    (b) processing the gas stream in one or more distillation columns to yield a light hydrocarbon stream, wherein the light hydrocarbon stream comprises ethylene and ethane;

(c) contacting at least a portion of the light hydrocarbon stream with a purged hydrocarbon adsorber to yield a loaded hydrocarbon adsorber and a non-adsorbed gas stream, wherein at least a portion of the ethane is adsorbed by the purged hydrocarbon adsorber at a pressure of from about 1,000 kPa to about 2,700 kPa to yield adsorbed ethane, wherein the non-adsorbed gas stream comprises recovered ethylene, wherein the recovered ethylene comprises at least a portion of the ethylene of the light hydrocarbon stream, wherein the light hydrocarbon stream is characterized by a temperature of from about −25° C. to about 30° C., wherein the hydrocarbon adsorber is characterized by an adsorption selectivity of ethane versus ethylene as determined by volumetric adsorption at 298 K and at a pressure of from about 1,000 kPa to about 2,700 kPa of equal to or greater than about 2, and wherein the hydrocarbon adsorber comprises a zeolitic imidazolate framework (ZIF) selected from ZIF-7, ZIF-8, or both ZIF-7 and ZIF-8;

(d) contacting at least a portion of the loaded hydrocarbon adsorber with a sweeping gas stream at a pressure of from about 50 kPa to about 150 kPa to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the sweeping gas stream comprises isobutane and/or nitrogen; and (e) contacting at least a portion of the unloaded hydrocarbon adsorber with at least a portion of the sweeping gas stream at a pressure of from about 1,000 kPa to about 2,700 kPa to yield the purged hydrocarbon adsorber and a spent sweeping gas.

22. A process for ethylene polymerization, the process comprising:

(a) polymerizing ethylene in a slurry loop reactor system to obtain a polymerization product stream;

(b) separating a polymerization product stream in a flash chamber into a gas stream and a polymer stream;

(c) processing the gas stream in one or more distillation columns to yield a light hydrocarbon stream, wherein the light hydrocarbon stream comprises ethane and ethylene;

(d) contacting at least a portion of the light hydrocarbon stream with a purged hydrocarbon adsorber to yield a loaded hydrocarbon adsorber and a non-adsorbed gas stream, wherein at least a portion of ethane is adsorbed by the purged hydrocarbon adsorber at a first pressure to yield adsorbed ethane, and wherein the non-adsorbed gas stream comprises recovered ethylene, wherein the recovered ethylene comprises at least a portion of the ethylene of the light hydrocarbon stream, wherein the hydrocarbon adsorber is characterized by an adsorption selectivity of ethane versus ethylene as determined by volumetric adsorption at 298 K and at the first pressure of equal to or greater than about 2;

(e) contacting at least a portion of the loaded hydrocarbon adsorber with a sweeping gas stream at a second pressure to yield an unloaded hydrocarbon adsorber and a recovered adsorbed gas stream, wherein the recovered adsorbed gas stream comprises at least a portion of the sweeping gas stream and at least a portion of desorbed ethane, wherein the desorbed ethane comprises at least a portion of the adsorbed ethane, and wherein the first pressure is greater than the second pressure by equal to or greater than about 400 kPa; and (f) contacting at least a portion of the unloaded hydrocarbon adsorber with at least a portion of the sweeping gas stream at the first pressure to yield the purged hydrocarbon adsorber and a spent sweeping gas.

23. The process of claim 22, wherein at least a portion of the sweeping gas stream and/or at least a portion of the spent sweeping gas is contacted with at least a portion of the light hydrocarbon stream during (d) contacting with the purged hydrocarbon adsorber;

wherein at least a portion of the non-adsorbed gas stream is separated into a nitrogen stream and an isobutane and ethylene stream;

wherein at least a portion of the isobutane and ethylene stream is recycled as a reagent for (a) polymerizing ethylene;

wherein at least a portion of the nitrogen stream is recycled to the sweeping gas stream;

wherein at least a portion of the nitrogen stream is recycled to a purge gas stream contacting at least a portion of the polymer stream;

wherein at least a portion of the gas stream is distilled into a light distillation bottoms stream comprising olefin-free isobutane, wherein at least a portion of the light distillation bottoms stream is recycled to the sweeping gas stream;

wherein at least a portion of the spent sweeping gas is recycled to the sweeping gas stream; and wherein at least a portion of the recovered adsorbed gas stream is recycled to an ethylene production process.

* * * * *